United States Patent
Dent et al.

(10) Patent No.: US 10,793,484 B2
(45) Date of Patent: Oct. 6, 2020

(54) MICROORGANISMS AND THEIR USE IN AGRICULTURE

(71) Applicant: AZOTIC TECHNOLOGIES LTD, Chorley, Lancashire (GB)

(72) Inventors: David Dent, Fleet Hampshire (GB); Dhaval Patel, Nottingham (GB); Gary Devine, Nottingham (GB)

(73) Assignee: Azotic Technologies LTD, Lancashire (GB)

( * ) Notice: Subject to any disclaimer, the term of this patent is extended or adjusted under 35 U.S.C. 154(b) by 377 days.

(21) Appl. No.: 15/747,425

(22) PCT Filed: Jul. 27, 2016

(86) PCT No.: PCT/GB2016/052289
§ 371 (c)(1),
(2) Date: Jan. 24, 2018

(87) PCT Pub. No.: WO2017/017440
PCT Pub. Date: Feb. 2, 2017

(65) Prior Publication Data
US 2018/0215675 A1   Aug. 2, 2018

(30) Foreign Application Priority Data
Jul. 28, 2015 (GB) .................................. 1513277.2

(51) Int. Cl.
C05F 11/08 (2006.01)
A01N 63/00 (2020.01)
(Continued)

(52) U.S. Cl.
CPC ................ *C05F 11/08* (2013.01); *A01C 1/06* (2013.01); *A01N 63/00* (2013.01); *C12N 1/20* (2013.01); *C12Q 1/689* (2013.01)

(58) Field of Classification Search
None
See application file for complete search history.

(56) References Cited

U.S. PATENT DOCUMENTS 8,304,215 B2 * 11/2012 Kim ........................ C12P 19/04
435/101
2002/0142917 A1 * 10/2002 Triplett ..................... C12R 1/22
504/117
(Continued)

FOREIGN PATENT DOCUMENTS

EP    1130115 A2    9/2001
EP    1714545 A1    10/2006
(Continued)

OTHER PUBLICATIONS

Examination Report relating to Application No. GB1801538.8, dated Nov. 27, 2019; 6 pgs.
(Continued)

*Primary Examiner* — Wayne A Langel

(57) ABSTRACT

A strain of *Gluconacetobacter diazotrophicus* (Gd) characterised by the presence of at least one nucleic acid sequence selected from SEQ ID NOS 1-10 or variants or paralogues thereof and/or the presence of a single plasmid of about 17566 bp in size. Such strains, exemplified by IMI504853, are useful in agriculture, in particular as they are able to colonise plants intracellularly.

20 Claims, 9 Drawing Sheets

Specification includes a Sequence Listing.

(51) Int. Cl.
*C12N 1/20* (2006.01)
*A01C 1/06* (2006.01)
*C12Q 1/689* (2018.01)

(56) References Cited

U.S. PATENT DOCUMENTS

| | | | |
|---|---|---|---|
| 2011/0225679 A1* | 9/2011 | Vessey | C05F 11/08 800/298 |
| 2012/0015805 A1* | 1/2012 | Goodwin | A01N 61/00 504/100 |
| 2012/0309000 A1* | 12/2012 | Kim | C12Q 1/689 435/6.11 |
| 2015/0101373 A1* | 4/2015 | Munusamy | A01N 63/00 71/7 |
| 2016/0355445 A1* | 12/2016 | Bobeck | C05G 3/90 |
| 2020/0048666 A1* | 2/2020 | Lynch | C12N 9/88 |

FOREIGN PATENT DOCUMENTS

| | | |
|---|---|---|
| WO | 03/020014 A2 | 3/2003 |
| WO | 2010/022517 A2 | 3/2010 |
| WO | 2011/144741 A1 | 11/2011 |
| WO | 2016/016629 A1 | 2/2016 |
| WO | 2016/016630 A1 | 2/2016 |
| WO | 2017/017439 A1 | 2/2017 |
| WO | 2017/017440 A1 | 2/2017 |

OTHER PUBLICATIONS

Rouws et al., "Monitoring the colonization of sugarcane and rice plants by the endophytic diazotrophic bacterium Gluconacetobacter diazotrophicus marked with gfp and gusA reporter genes," Letters in Applied Microbiology, 2010, pp. 325-330, vol. 51.
Dawson et al., Data for Biochemical Research, 1986, 3rd ed., Oxford University Press (New York, NY: 1986), p. 289.
Adriano-Anaya et al., "Hydrolytic enzyme activities in maize (*Zea mays*) and sorghum (*Sorghum bicolor*) roots inoculated with Gluconacetobacter diazotrophicus and Glomus intraradices," Soil Biology & Biochemistry, 2006, pp. 879-886, vol. 38.
Bertalan et al., "Complete genome sequence of the sugarcane nitrogen-fixing endophyte Gluconacetobacter diazotrophicus Pal5," BMC Genomics, 2009, pp. 1-17, vol. 10, No. 1.
Caballero-Mellado et al., "Limited Genetic Diversity in the Endophytic Sugarcane Bacterium Acetobacter diazotrophicus," Applied and Environmental Microbiology, 1994, pp. 1532-1537, vol. 60, No. 5.
Cocking et al., "Intracellular Colonization of Roots of *Arabidopsis* and Crop Plants by Gluconacetobacter Diazotrophicus," In Vitro Cellular & Developmental Biology Plant, 2006, pp. 74-82, vol. 42.
Demesure et al., "A set of universal primers for amplification of polymorphic non-coding regions of mitochondrial and chloroplast DNA in plants," Molecular Ecology, 1995, pp. 129-131, vol. 4.
Doyle et al., "A Rapid DNA Isolation Procedure for Small Quantities of Fresh Leaf Tissue," Phytochemical Bulletin, 1987, pp. 11-15, vol. 19, No. 1.
Eskin et al., "Research Progress and Perspectives of Nitrogen Fixing Bacterium, Gloconacetobacter diazotrophicus, in Monocot Plants," International Journal of Agronomy, 2014, pp. 1-13, vol. 60, No. 10.
Fuentes-Ramirez et al., "Colonization of sugarcane by Acetobacter diazotrophicus is inhibited by high N-fertilization," FEMS Microbiology Ecology, 1999, pp. 117-128, vol. 29, No. 2.
Giongo et al., "Two genome sequences of the same bacterial strain, Gluconacetobacter diazotrophicus PAI 5, suggest a new standard in genome sequence submission," Standards in Genomic Sciences, 2010, pp. 309-317, vol. 2, No. 3.
International Search Report and Written Opinion from International Application No. PCT/GB2016/052288, dated Nov. 17, 2016; 10 pgs.
International Search Report and Written Opinion from International Application No. PCT/GB2016/052289, dated Nov. 11, 2016; 12 pgs.
Koressaar et al., "Enhancements and modifications of primer design program Primer3," Bioinformatics, 2007, pp. 1289-1291, vol. 23, No. 10.
Krumsiek et al., "Gepard: a rapid and sensitive tool for creating dotplots on genome scale," Bioinformatics, 2007, pp. 1026-1028, vol. 23, No. 8.
Pedraza, "Recent advances in nitrogen-fixing acetic acid bacteria," International Journal of Food Microbiology, 2008, pp. 25-35, vol. 125, No. 1.
Reis et al., "Nitrogen fixing bacteria in the family Acetobacteraceae and their role in agriculture," Journal of Basic Microbiology, 2015, pp. 931-949, vol. 55, No. 8.
Tomlinson et al., "Loop-mediated isothermal amplification for rapid detection of the causal agents of cassava brown streak disease," Journal of Virological Methods, 2013, pp. 148-154, vol. 191.
Untergasser et al., "Primer3—new capabilities and interfaces," Nucleic Acids Research, 2012, e115, pp. 1-12, vol. 40, No. 15.
Zhang et al., "Ramification Amplification: A Novel Isothermal DNA Amplification Method," Molecular Diagnosis, 2001, pp. 141-150, vol. 6, No. 2.
Receipt, Budapest Treaty on the International Recognition of the Deposit of Microorganisms, Microorganism ID reference: AZ0019, Accession No. IMI CC No. 504958, issued pursuant to Rule 7.1 by the International Depositary Authority, dated Jan. 29, 2018.

\* cited by examiner

SEQUENCE LISTING

<160> NUMBER OF SEQ ID NOS: 68

<210> SEQ ID NO 1
<211> LENGTH: 630
<212> TYPE: DNA
<213> ORGANISM: Acetobacter
<220> FEATURE:
<223> OTHER INFORMATION: Glutathione S-transferase (EC 2.5.1.18)

<400> SEQUENCE: 1

```
atgacaaaat tatactattc tcccggcgct tgctctttgg cagggcatat tttgctcgaa      60
gagttgggaa gaccatatga gttgaaattg acgcccgttg gagacgaagg cacgggaagt     120
gaagagtttc taaaaataaa cccgcgagga agggtgcctg ttttaattga tggtgcggaa     180
ataattaccg aaagccccgc aatcttattt tatttatcga gttcattttc agacggaaat     240
ttctggccaa aatcagtttt ggagcaagcc cgctgctggg aatggtttaa ctggttatcg     300
agcaatgtac actcggttgc ctatgggcag gtgtggcgac caggacggtt cattgatgat     360
gagcgtcagt ggaataatgt tatttcaaaa gggaaaaata accttcatga atttagtgat     420
gtaatagaaa ataatatctc cgggaaaacg tggtgtgtgg gtgaatcgta ttcatgcgtt     480
gatccgtatt tgtttgtttt ttattcttgg gggaaagcca tcggattgga tatggaatcc     540
tctttcccgg cgtggtcgcg tcatgcagcg cggatgctgg agcggttggc cgttcaaaac     600
gctttacggc aagaaggttt gatctcgtaa                                      630
```

<210> SEQ ID NO 2
<211> LENGTH: 729
<212> TYPE: DNA
<213> ORGANISM: Acetobacter
<220> FEATURE:
<223> OTHER INFORMATION: O-methyltransferase (EC 2.1.1.-)

<400> SEQUENCE: 2

```
ttggatgcct ctcgttttcc ttgcggagtc atcatgacca ttcctctctt tcgtccgcaa      60
ttcacaccgc agattcaacg tgcgcttgat cgcctttatt ccgagacact ctcgcaagat     120
ccagcgatac gccaattggc gcaagccaaa ggactgacac atgacgggca acgcggtttc     180
tacgaagcca tgaaagatgc cagactaccc gttacgccag agttcggcgc cctgctctat     240
attctggcac gcagcaccag agcccaacat atcatcgaat cggcacgtc cttcggtgtt      300
tcaacattat ttctcgcagc ggctttacgc gacaatggcg ggggccgact ggtgaccctcg    360
gaacttatct cagacaaagc agaaagggct tccgccaatc tgcgggaggc aggactggca     420
gacctcgtag acattcgcat cggagatgcc cgcgccacgt tatcgcgtga tcttcctgag     480
tcgatcgatc tgatcctgct ggatgcgact aaaggactct acctcgatct cttactcctg     540
ctggaacctg cattacgaaa aggtggcctg tgatcagcg atcgcgccga tctcgatggt      600
gacgacggcg gtcgcgcagc agcctacctt acctatctga caaccccggc taacggatat     660
cgcatcgccg gcatcactac acaggcgttg ggacaaacct tcgctcacga tgtggcggtg     720
cgcacctga                                                              729
```

<210> SEQ ID NO 3
<211> LENGTH: 462
<212> TYPE: DNA
<213> ORGANISM: Acetobacter
<220> FEATURE:
<223> OTHER INFORMATION: Transcriptional regulator, TetR family

<400> SEQUENCE: 3

```
gtgggaatag ccacgctcta ccaatacttt gagaacaagg agagcgttgt cgcggcactt      60
agtcgtcggg tacgggaaac actgctccat gatgttgcgt cattactcga aaccgcttgt     120
tcgttgccac tttccgaggg tgtgcgctgt ctggtcgtcg ctgccgtgaa ggcggacaag     180
agccgtccat cgcttacggt ccggcttgat cggttggagg aggctctttc tttggaagcg     240
gatcatctgc tggtagcggc tgagctttgc acggttgttg cgtcgttcct caagtgccag     300
ggaattattc aggagaacac tgcaaaaatt ctggcagatg atctgtgtac gataacaggg     360
gcacttattg acgctgcaca caatcgacag ataccta tcg atgacttgct aattgaccgt     420
attacgcgaa ggctggtcgc gattattcag agcgcgcttt aa                        462
```

<210> SEQ ID NO 4
<211> LENGTH: 522
<212> TYPE: DNA
<213> ORGANISM: Acetobacter
<220> FEATURE:
<223> OTHER INFORMATION: RNA polymerase ECF-type sigma factor :: RNA
      polymerase ECF-type sigma factor

<400> SEQUENCE: 4

```
gtgggacagc cggacaaata tttcgagctt ttcgcgatac atcgcaccga tcttgtgcgt      60
ttcgccagag gtatcatgag agatgatagt ctggcggaag atgttgtaca ggatgctttt     120
ctgcggctga ctactgtaac agtggcacag gaccgcgttc tttcggatcc tctgaattac     180
gtttaccgca ttattcggaa tctggccttt gaccgttatc gacgacggca attcgaggcc     240
ggattgtttg accatggggt agatagttct tccgaaacaa tcgaagcgga tgcccctaca     300
ccggaaggtg aggcttcagg gaaatccgac atgcgggcaa tgcgcgccgc tatggcggaa     360
ctgccagaac ggacgtgcgt cgcattggaa atgcatctgt tcgacggacg aaagctacgg     420
gaaatagcgg ctcatttagg tgtttctatt gggatggccc actcccttgt cgcagtgggt     480
atggagcatt gccgcaaacg tctttccaca cctgaaacct ga                        522
```

<210> SEQ ID NO 5
<211> LENGTH: 984
<212> TYPE: DNA
<213> ORGANISM: Acetobacter
<220> FEATURE:
<223> OTHER INFORMATION: FecR family protein, COG:Fe2+-dicitrate sensor,
      membrane component;

<400> SEQUENCE: 5

```
gtgagcgaag acttcaatcc aacaacggcg gttgagtgga aaatagccct ttcagaagag      60
cctgacgatt ctgtgctcag agaacgcttt gaagcatggc ttgctgccgc agaggatcac     120
cggaaagagt ggcaggaact tacgcaggga cttgagaatt ccgccagat tggcccgctt     180 tatcgtgaga atgggtgcc ttcatcaagt ggggcacaaa atactgcgtc aaaacaaggt     240
aggctcaaag gaagacctgc taattttgtt aggttttcag ttgctgcatt tgcggctgct     300
gctgccgtta cattggtatg gtcctctgac cttctgcttc gattacaggc cgattacgcc     360
acaggctcgg cagaaacgcg aacagtcagt ctccccgatg gtagtgaatt gaccctcgcg     420
ccgcgaagtg cggtaaaaat gtcttactct gtagagaaac gggatattcg tcttttaaag     480
ggagaggcgc tcttcacggt tcgacatgat atggcgcgac cttttgaggt ccacacagac     540
aaattcaccg taacggacat cggaactatt tttgacgtca gaatgtctca gggcgaggaa     600
gaagtctctg tccgggaagg agaggtccgg gtgcaggatg tttccggtgg atttcataat     660
```

-continued

| | |
|---|---|
| ctcgatgccg gaacgtggga gcggattaga actgtaggca atggagtgag cgtcactcat | 720 |
| gggagcggct ctccggaaga tgtgggcgca tggtcagcgg ggcaaattat tgccaaggaa | 780 |
| aacagcgtgt ccagcgtcgt ggaaaggctt aggccctact accgggggt tgttgtcctt | 840 |
| tatggttctt cctttgggga gaagtcactc actggtgttt atgacgcaag tgacccggtt | 900 |
| ggcgcatttc gggcgatcgc agccgcgcat catgctcaga tgcatcaggt ttcgccatgg | 960 |
| ctgacaatat tggccgcacc gtag | 984 |

<210> SEQ ID NO 6
<211> LENGTH: 2604
<212> TYPE: DNA
<213> ORGANISM: Acetobacter
<220> FEATURE:
<223> OTHER INFORMATION: Ferrichrome-iron receptor

<400> SEQUENCE: 6

| | |
|---|---|
| atgaagggtg cggttgcatt gcattcgcaa ttgtggcggc tcatacgaat gggaacggat | 60 |
| aaggtgatga cgattgatga tagaatgaag cggtgtgggc ggcaggtggc gtggcttatc | 120 |
| gcgctgggta gtacgacgtt tctgaatgcc gctgtgacga aaagctatgg tgcagaacct | 180 |
| tcccaaagtg ctcgggccgt cagatcattt tccattccgg cccaatctct tgaagatggt | 240 |
| ctcgcaaggt tcggacagca aagtgggtgg caggtttctg ttgacggaaa tcttgcaaaa | 300 |
| tctctgacaa cgcacggtgt tagcggtacg atgcatctg ctcaggccct caatgcgatc | 360 |
| ctgtccggga ctggcctgac atacacgatc aggggtggcc gaaccgtcgt gctgacgaaa | 420 |
| gcagtagcca acatcacgct tggtccggtc cgtgtcggag aaccctcgc cgtcaggat | 480 |
| ccaacagggc cgggtgtcgg ctacttcgcc gaaaacacaa tggttggtac aaagacggat | 540 |
| acgcccatca cggaaatacc gaactcagtc tacgtcgtga ccaagcagtt gatgaccgat | 600 |
| cagcagccgc agaatatcct acaggctttg cgttacactc ccggcatcta ctctgaagcc | 660 |
| ggaggaacga caaatcgcgg atctgcccag aatgacaaca tgggcattta tcagcgtgga | 720 |
| tttctctcga gccagttcgt ggatgggttg atgacgaatt cgtatgccgc cgccgagcca | 780 |
| agctttctgg accgtatcga ggcgctcaac ggtccagcat cggtgatgta tggccagacg | 840 |
| acacccggag gaatggtcgg tatgagcctg aagaaaccca ccgaaacgcc gctgcatcag | 900 |
| gtttcgctag gcttcggaag ctggggacgg tacgaggcaa cgttcgatgt cagcgataag | 960 |
| atcacgcagt ccggtaatct cgctatcgt attgcagcca tcggagtcac atcgggcact | 1020 |
| caggaagacc gaattgatta tcatcggtg ggtgtacttc cttcaatcac gtgggatatc | 1080 |
| gatcccaaga ctcgcctcac tctacttggt agttatatgt acacgcctgg ctcagggagc | 1140 |
| accagtggtt atccggtcct cgggactctt attcacaatt cggaaattcc acgaatctca | 1200 |
| cgaagcacat ttatcggaat acctagttgg aacactatgg agataaggt cgggatgttc | 1260 |
| gaatatcaat ttagtcataa atttaataaa tttattgagt tcaatcagac gtttcgcgta | 1320 |
| gagaattcca acgttcatga gtcaaatatc accgatgtaa cacctgtaga tgttgaagga | 1380 |
| aaatggacat atttttatcc ttggaaacaa aattatgaaa acacaactga ggtacttgat | 1440 |
| actcgcttag gggcggtt tctaactggt cctgtacaac atacatgggt catcggttct | 1500 |
| gatttccgca attatgacta tcattatact gagctcatcg acgacggtgc gacaatcgtt | 1560 |
| gtgcccactc agcacccgac atcaaactat tccccatgta taagtttaac ctccgcgaag | 1620 |
| tgtgacgcct tcgcgggaat aaacccagac tataactcgt ttcaggaggg cgtgtatttt | 1680 |
| caggaccaga taaaatggca gcgcctgtcc gttctcttgg gtggacgcca agattgggtt | 1740 |

```
aattcatcta ataaaaatta cagtgtaacg aactttatg gaaacgtcag cacccgcgtt      1800
aataacactg ctccacaccc tcaatcggcc ttcacctgga gagctggtat aatctataat      1860
tttgactttg ggcttgcccc gtacttcagt tacgcaacat cctttgtgcc acaaggaggt      1920
acggattggc agggtaagat tttcgcgcct ttgagcggaa agcaactcga agccgggttg      1980
aagtataaag ttccaaacga agatatcctc ataacggcat cagcattccg aattgatgaa      2040
gaccactatc ttatcagtga tcttgttcac acgggcttta gcagtgacgc gggaacggta      2100
cgctcgcagg gtttcgaggt ttccgccagt gcgaacatta ccaaaaacct caaacttgtc      2160
gcctcttaca catatgagga tgtgcggttc agaaagaaca atttggccgt aaattcggtc      2220
gatcccgtca cgctaacata tggagcaaag gtaagcgaga atggaaaatt cgttcctcga      2280
gttcctcgga atatgtttaa tatgtttctt gattacacct ccacgacgc cccattgaag      2340 ggtctcggct ttaatggagg aattcgctac accggtttta cctatgcgga ctatgtggag      2400
tcttacaaaa cgccggcgta ttatctgttt gacattggcg cacactatga ttttgaggaa      2460
ataatccctt ctctcaaagg tctgcgtgcc cagttggcaa tctcaaattt ggccaataaa      2520
tattatatta cttcgtgcaa taccgccata tgtactctcg ttatgctcg aaagttttac      2580 ggtaacgtga cgtatagctg gtga                                            2604

<210> SEQ ID NO 7
<211> LENGTH: 3066
<212> TYPE: DNA
<213> ORGANISM: Acetobacter
<220> FEATURE:
<223> OTHER INFORMATION: Reverse transcriptase family protein

<400> SEQUENCE: 7
gtgacgcccg aattgctcct ctccaaggtg cggctgctgc ggtcgcccaa tgacgacggc        60
gcgttcttcg acctagtcgg cagtgttctt aattggtcct gggaggaaag agacgaacgt       120
caattcgccc gcttcaagca gcgcgcgggc atccctgagt tcgatggcgt cgcccttcca       180
cagggtttgg ttgcagctgg cttcttctcg aacatcgtgc tgcttgattt cgatcggatc       240
gtcatcggac agattgggag agaagttaca aacggagtgt ggctccggga cgcctgccgg       300
tacgtcgacg acattagact gaccataaca actgcaccag gtattgaccc aagagaagct       360
caggcgcgtg taatggcgtg gcttgggcaa ctcctcacgg ggagctgtcc gggcttggaa       420
ttctccccgg agaagacgtc aactgcgtcg gttggaggcg agcagatgcc gctggttcgc       480
caatcccgaa agatggagcg catccagacc gcgatttccg gcggcttcga tgccagtggt       540
ggcgaggagg tgatccacgc gatcgaagcc ctcgtccgat cccagctaac gatcaacagc       600
gtcgaagagt cgcctacccc tcccggcttg agagcggtac ccgatgtcaa agacgagaca       660
gtcggtcgtt tcgctgctgg tcggttcaga aaaacctttc gttcattgag gccactactc       720
gatgatcgac cttacatgga gattgctgaa ttcggggagg agacgttccg gcgcacccga       780 cttcgcaat cggagcttga cgaggaagca gcgcatttg cgctaatcct agtcgaacgg       840
tggatactcg atccttcgaa tgtgcggctg ctgcgcgtcg cactcgacct ctggccgtcc       900
cgccaactcc tcaaggaagt actgaaactc tttgagccct atcttgtcgg gaagatcagg       960
gcaatcacta gccggcaagt tgcatactac tgcctcgccg agatatttcg agcaggggcg      1020
accgagacgg gcttcattga cgatccgagt tgccttcccg ctgccgtcga tctcgccggt      1080
tatagatctc tgcttctgga ggccgcagta cgagtggccc ggggcgaagc cgaacgtgtc      1140
```

| | |
|---|---|
| ccgtggtatc tcgcgcaaca agcactgctt tacattgcgg tccacgatcc ccgggctatc | 1200 |
| caagatcgag gaatttcaaa gaccaatcga tcctattggc gcctcgtctc atttctgaaa | 1260 |
| ggcgaacgcg acgtctcttc agatcgcgaa ttcgcagtag ccgcggtggt gagccgcagg | 1320 |
| tcgttccttt cgaatgatca ggccgtggat ctcgtcggtc ggatgctcac gccagagcgg | 1380 |
| ttcgccgagg tggccgcgcg cgacatagaa ttcgcccgcg atctctttcg cgccgtcgac | 1440 |
| cgacacctca ccgttccggc aggcattgcc gaggacttgg gggtcgccga atggtccatg | 1500 |
| tcagaggaaa tgagctctct gcaaagctat atccaaggca aagggcctct gaatccgcta | 1560 |
| cgcaatgaga tcggcgtact cagttttgca gagaaattca tctcccatct ccaagaagga | 1620 |
| aatttgccgg aagtcgtgac gccgtcgacg acgcagatag cggtacagca agtgggcaaa | 1680 |
| tatgtccgcg tcgaacgggt gatcttcaga tcggcccaga caacgccgac ttaccggtct | 1740 |
| atttatactg ctcccagatg ggcgccggaa tctcaacgct ggcgctttca gctcggttat | 1800 |
| ttacttcgct tcattcttac tgccagaata gacttcagcc ttccagttag gccgccatcg | 1860 |
| tggaaggaag gtaaacacat ctatcggcct accagaagtc actggtttca gcggcaatac | 1920 |
| ggcttctata atgggcatga ggccttcggg gacgattggc tacccatttc gcagttcact | 1980 |
| caggatcttc tcttcgatct gctcacctgg cccggctgcc gcacaagtag cccggatgtc | 2040 |
| gatcagttgt ccctggatga aacggctgct cgaatccgcg cagctctcgt agaagccacc | 2100 |
| gctgcgattg gcccggctac aggaaccctg atgctcaaga tcgatgcacc tattccaggt | 2160 |
| accacatcga agggggcgccc gcttcgggcc tgcgtcgtcc agtcgatcat gcccgaagca | 2220 |
| gaggacttct cggctgccga tctggagatg cgctcgccgg cccttcgacg aaagcaccgc | 2280 |
| aaacatctgt ccacggcatt ggcggcggtt gagaagatgt tggatcttcg cgagactcat | 2340 |
| aagccagcca gcaagcgtct cgactggctc atcctaccag aactgtctgt tcacccggat | 2400 |
| gacgttgcca cccacctcgt gccgttcgcg cgagcgttca agaccgcgat cctggtcggc | 2460 |
| atggcctacg aacaagtcgt cacggggagg ccgctgatca actcggccct ctggattatc | 2520 |
| ccgaggatgg tgcggggcat gggcctacag acggtgatca gacggcaggg aaaacagcac | 2580 |
| ctctctccga tggaacagaa gtacgtcaaa ccggtcgaac tgatcaccgg attccgcccg | 2640 |
| tgccagtggc tggtggggta cgaatggtcg aacaatccgg ccaaagacgc actttggctc | 2700 |
| accgcgtcca tctgctacga tgcaacagac ctgaagctgg cgagcgatct tcgtgatcgc | 2760 |
| tcagacgtgt ttgcgatccc agccctgaat ctcgacgtcg gcaccttcga tcagatggcg | 2820 |
| caggcgctgc attatcatat gttccaactc gtgctgatcg cgaacaacgg agcttatggg | 2880 |
| ggcagcaatg ctcacgttcc caaggggag gcctatcaac gccaagtgtt ccatacccat | 2940 |
| ggccagcccc aggctacaat ttcctttttc gagatcgacg atatcgaggg catgaagcag | 3000 |
| agacacaagc tcggcgctgg gaaggaaggc gggtggaaat atccacctgc cggctgtcaa | 3060 |
| gtctga | 3066 |

<210> SEQ ID NO 8
<211> LENGTH: 513
<212> TYPE: DNA
<213> ORGANISM: Acetobacter
<220> FEATURE:
<223> OTHER INFORMATION: DNA topology modulation protein

<400> SEQUENCE: 8

| | |
|---|---|
| ttgatgcgct tgttcgtgac ggggccaact ggcagtggaa aatcaacgct ggctgcaaag | 60 |
| ttggctcaaa gggcagctat accactgttc ccgctcgatg aaattcattg ggttcgccat | 120 |

```
ctctccgggg attggcggcg cgatcctgtt gaacgcctgt ctatgctcgg agagattgta      180
cagctcgatg cctgggtcat cgaaggcgtg cagttcaaat ggactgatat agcgatagaa      240
cgagcagact ggatcgtcgt cctcgatcca ccacgttggc ggaacatcgc tcgtatcctg      300
cgccgtttcg tcaatcgccg atgctttact ggggcgggc accgtggaac ggtaaaggct       360
ctattggagg agatgcgttg gtcagccgac tactatggtc atgaacgcgg tatgctgttc      420
gagaagattg acaatcgcc agacaagctc atcgtcgtac atgacgacaa gggcgaacgc       480
gctttgaccg aggctgtatt cgcgactgcg tga                                   513
```

```
<210> SEQ ID NO 9
<211> LENGTH: 2352
<212> TYPE: DNA
<213> ORGANISM: Acetobacter
<220> FEATURE:
<223> OTHER INFORMATION: Cycloisomaltooligosaccharide glucanotransferase
      precursor (EC 2.4.1.-)

<400> SEQUENCE: 9
```

```
atggcatatt ggatcaggct ctcgctggcc gtgtggccgc ccgatcagca acgttgtagc      60
gaaggccgcg taatgcgccg ctatcttttc acaaccattc tctcgctctt accgtccctt     120
gcggcggcgg catccctcca aggtccgatt gtttcgcatg tgcgggatga tcgggctttc     180
taccaggcag gcaatgtcgc gatgatttcc gtggaactga ccccactagc cgcttggacg     240
ggaggccatg tggatctagc gatatgttcg cgtgggcaag tcgtgggcac gattcagagc     300
caagcggtca ccagcatggt ggctggggcg gaccagacac ttcactatcc cgtcaccgtt     360
cccagtctcc atgctcatgg gtatcagttg ctatcgcgg ccctgaacaa tggggacagc      420
gggacagcgt cctgtaccgg gacaggcagc acttccacgt cgccggccga tgtggcgtca     480
ggcggcatca acgtggccgc gaatgcctgg aagacatca acgaagcatg ggtcgacgcg      540
ccgacgctcg gcaacgtctc gcggcccgg tgatggata tctcagcca gtatcacatc        600 aacgcggtgc aattttacga cgtgctgtgg cgacatgacg agccgtattc atccgccccg     660
cagtggccga acctggaagg cgtaacggtc acaaggacca atcttcaggc ttatatcagc     720
gcggcgcata gccgcggcat ggtggcgctc gcctataatc tctggaacgg agcctgggcg     780
gactatgcaa ctgtcaatcc gaaggtcacg gcggcaatgg ggctctatgc ttcgtccgga     840
cagaaacacc aactgaccaa cggcggggc tggctgtcct gggggtggtc gaccgaccat      900
attgctgaaa tgaacccgtt caatggcgac tgggccagat ggctaaccag ccagatccag     960
aagaccatgt ggaatttagg attcgacgcc gcgcatctgg atacgttggg tgaccctggt    1020
ggtcagcaat atgacggcga gggccatccg ttacctgctt taggaacgat tctggcagac    1080
tttgcgaata atgtacaggc tcagaccggg gcaccaactg acatcaacgc cgtttcgggt    1140
tggaatacca ccgaccttta cctacgcggt acgggaccca acctgtatat cgaaccccat    1200
cccgaattcg aaacacgcc gggctacgat gattcccgaa gcttatggga catcaaacag    1260
aaatatacgt cgcgcccgct gatgacggcg ttttatccgc agcaggtcca gagcggttcg    1320
ctgagcacgt cctttgccgt caagggtgag agtgtgaagg tttgcgaccc gacgttaaaa    1380
tccggatgca tagccaataa cctcggcatt gagttgttgc tcggccagat tgcgctcaat    1440
ggaggctcca atattactct tggtgatttt gatcatctga taccggggcc atatttcccc    1500
cgtccgacct taagatcga cggtccattg cagcaatatc tggcggatta ctacaactgg    1560
tgggtcggaa tgcgcgatct gctgcgtgtc ggcgtcatct catccaatga gagggagtcc    1620
```

```
atccggaatg gaaacggagc cagtatcggc caaccttatg cccaaccggg aaccgtctac    1680
tatcatcccc tgatacgcgc tggcatcgct ggtgaattgg cgctcacaaa catgatcggg    1740
ttgcattata atcggattga cgaccctgac ggcaaaaaca atccgacccc ggtgaacaac    1800
ctgtcgatcg agatggaatt ctgggaaaga agcacaccgg gggcattgta ctatagcgcg    1860
cccgacatca accacggctt cccacagccc ctcacctata ggctgaacgg aaacggtagc    1920
gtgatgttta cgctaccgac tctcaagacg gtggcgcttg tttggctgga aggcaccaat    1980
ttcaccacta cgaccgatta acgatcggt acggcgcagg atgtgagggg tggcacagca     2040
aacttctgga cgaacggcag cggagaggat gctaccggat atcgtggctg ctgtggtcgc    2100
tccgcacgct gggacagcat cgatttcgga gcgggtgtgt caacgctaac gatggtaacc    2160
cgaagccaac tcggcggact ggtcgaattt cgcctggatg cacctgatgg accagtcatc    2220
gcccgtaatt atgttcctgc gtctagcgcc acgacaacaa ccactcaatt acgcaggcca    2280
gtattcggga cacataccgt cttcgctaaa attcctggtc gcgagattac gctgatatcc    2340
tggaagccat aa                                                        2352

<210> SEQ ID NO 10
<211> LENGTH: 855
<212> TYPE: DNA
<213> ORGANISM: Acetobacter
<220> FEATURE:
<223> OTHER INFORMATION: Methyltransferase (EC 2.1.1.-)

<400> SEQUENCE: 10
atgatggcta acgacaatac cactgaggtg gttggtgcat ttgcggtaag tcatcccaac      60
ttggcgcaag gttttacttt tagtaacagc agtcaactag atacgattgc ttctactatt     120
cataaaagcg gtttggagac ttatgaagct ccgacaacta atataattat cgaactgatc     180
aggagttcgt ctggtcttat tttagatgtg ggagcgaata ccggtctttt tacgctagtc     240
gccgcagcag ccaacccccct gatccgcgtc tgctcttttg agccgcttgc gagtattcgt    300
gaacttctca agagcaatat tgctctcaat ccggagcttg catcacgtat cgctgtcgag     360
cctgtcgggt tatcgaatga acggggcact ttcacttttt acgaaacgat caacaatcgt    420
ggctttgtca cgacgagttc atcgcttgaa aaagcacatg cagagcgaat cggcgatttg    480
tacgtcgagc gcactatcga gacccggaca cttgatgaat cggagaaaac gctcgggaat    540
gcgagcgttc cgttcgtcaa aattgacgtt gagggacatg agcatgccgt tatctccggt    600
ggccgccact ttatcgccaa gcaccgcccct tttcttactc tcgaagtcct gagagaggct    660
aacactttga gtctggacca gttggtgacc gagtccaact accttgccct ggcaatggca    720
cccgacgaat tgcggcagtg cgagcgttta cggtttcatg acgacgcctg gaatcatctt    780
ttggtccccg ccgaaaaagc ggaacggcta ttttcgctct gccgccgact tggcttgcaa    840
atcgggatcc gctga                                                      855

<210> SEQ ID NO 11
<211> LENGTH: 744
<212> TYPE: DNA
<213> ORGANISM: Acetobacter

<400> SEQUENCE: 11
atgtcgaatt ccgagcgccc aatgcgcgat ttgtcggacc tggcaaaaaa ccgacaaata     60
gagccgatgg ttatcaggct acgagaagta gtggatcgga ccggaggcgc gaaagctgtg    120
```

```
gccgcacgca cggacatccc tctcagcaca ctttcaggtt acctgtcggg tcgggaactc      180
aagctttccg tcgcgcgcaa gatcacgaaa gcctgcggtg tcagtcttga ctggcttgcg      240
gcaggagagg acggacctgc ggcccgggaa ttcggcaatg cccggcaggc gggtcccgag      300
tcggtcgagt ttctgaatta cgacgtcatt ctctccgccc accagggcgt cgacggggat      360
agttcttata tcgaaacgag aatatcgata ccgcgggatt ttctcccttt gtccattcag      420
tccaatacgg acaacatttc ggccgtcacg gcgaaatgcg acagcatgaa tccgatcata      480
gacgatggag acattctttt aataagaacg gatgtgcata cgctcacaag tggcagcatc      540
tatgccctgc gggtagaaaa cacccttctg tcaggcgtc tgatcctcaa gaccaacggc       600
aacgtccagg tcatcagcga gaacccgcgt tacccgaccg aggaactgaa cgccgaggac      660
gttcgcagga tggtccagga cgacggcttt ccggccagga tcatcggccg ggtcatctgg      720
cgcgccggta gcctgattcc atag                                             744

<210> SEQ ID NO 12
<211> LENGTH: 2331
<212> TYPE: DNA
<213> ORGANISM: Acetobacter
<220> FEATURE:
<223> OTHER INFORMATION: outer membrane heme receptor

<400> SEQUENCE: 12
atgcgcatcg tcctcttgcc ctgcctcgtc gcgacctcaa taagtatgtt ggcggtttcc       60
gcatcctatg cttgggcgga caatagcccg tcgcccccca ggacgaacaa acaggccaaa      120
tcgcggccgt tacatgcgca ggggacgcgc aaagcgggca cgccatcac cagccaggat       180 gaagcggtgg ctgtcgtggg aacacgtgag acatcgcatg ggatggagca gagcgttacc      240
cgtgcgacga tggacaagtt cgtggcgggg accagtcccc tgcagattct gtcggccacg      300
acaccgggtg tcaatttgc ctcggacgac ccgttcggcc tggatacatg ggcgaacaca       360
ttttatattc gcggctattc ccaaagccag ttgggcatca ccctggacgg tatcccgctg      420
ggcgatgccc agttcatcaa ttccaacggc ctcgatatca atcaggcgat catccagaac      480
aatatcggtc gcgtcgacat gtcgcagggt ggcggtgcgc tcgatgtcat gtccgtcacc      540
aacctgggtg gcgcgctgca atattattca ctcgatccgc gcgacaaggc tggtggagac      600
atttcacaga cgttcggcag caaccagacc tatcgcacgt acgtcagcgc ccagagcggc      660
aagctcaatc ccagcgggac gaagttctat gcgtcgtacg cgcgcaccga tgccgggaaa      720
tggaaaggcg ccggggacca gttcaacag caggcgaatt tcaagatcgt acagccgctc       780
gggcgttacg gaaaactgtc cggattcttc aattattccg aattcgacca gtataattac      840
agcgatttga gcctggaaat catccagaag ctcggccgga acgtggatta tttctatccg      900
aactacaaag ccgcgtatca ggctgccgag gggatctatc ccgcaggcta tgccaaggtc      960
ggagatgcca tggacgtctc ctattacgat ggtggccagg accagcggaa ttatctttcc     1020
ggcatcacgt ccacgatcga cctgacgtcc cgcctgcatc tgaagacggt gctgtacgac     1080
cagcaatcgg cggggggacta cgaatggacc aaccctatg tgtcgtcgcc ctcgggcgcg     1140
cccatgatcc agcaggtcgg gcacacatcg atgacgcgcg tgggcgggat tggcgcggtg     1200
cagtaccaga tcgccaatca ttcgcttgaa accggcgtct ggtacgaaaa caacggatat     1260
agctgggcgc aacggtacta caaccagccg cttctggggg agggtacgcc ccgaagcgcc     1320 accgaccgt acaacgatcc gttcgccacc gcatacgcca tgaccttcaa taccaacagt     1380
tttcaatatt acctggaaga ttcctaccgt atcttgaaga cgctgcgggt gcacgcgggc     1440
```

-continued

```
ttcaaatcca tgctgacgac gacgtcgggc ggcgcatcct ataacaatcc cgtctatacg    1500
ggccaggaca ccctgcccag tggcagcctg accaccgcca gcgccttcct gccgcatgtc    1560
agcatcaact ggaatttcct gccccggaac gaactgtttt tcgacttcgc ggagaacatg    1620
cgcgcattca cctataatac atggcagagc gggaatgcat ggggagtcaa tgagatgccc    1680
cagaacctga agcccgagac caccttcaat tacgaggtcg gttatcgata taattcccgc    1740
ttcgtcacgg gcctcgtcaa tctgtatcat atcgattaca ggaacggct ggccaccatc    1800 accaccggca gcctggtgaa cgcccacaat acctatatca acgtggggaa catggcgatc    1860
tggggtgccg atgccggcgt gacggtgcgc ccgctgccgg gcctcgagat cttcaacagc    1920
gccagctaca acaaatccac ctatgggcag gatgtatcca gcggcggggt aaattatccc    1980
atcagcggca agcaggaggc cggctatccg caatggatgt acaaggccaa cgtctcgtac    2040
aggtatggca acgcgaaggt caacttcaac gtcaactata tgggaaagcg atacatctcg    2100
tacatgaacg acgccgccgt gaacgggtat tggctggcat cgctgtcggc gacgtatatc    2160
ttcaaaacca ttccccatct ctctcagctt gaattcaatt tcggcgtcta aacctgttc    2220 aaccaggaat atatcggcgg catcggcggg ttctcactgt ccggtgacac gcagcaactc    2280
tttgccggcg cgccacgcca gttcttcggt acgctgcacg cacggttcta g          2331
```

<210> SEQ ID NO 13
<211> LENGTH: 1812
<212> TYPE: DNA
<213> ORGANISM: Acetobacter
<220> FEATURE:
<223> OTHER INFORMATION: Levansucrase

<400> SEQUENCE: 13

```
gtgacggcgc ggtcgtggtt gctctgcaat ctgaagagtt tccttcagga ggatggaatg      60
gcgcatgtac gccgaaaagt agccacgctg aatatggcgt tggccgggtc cctgctcatg     120
gtgctgggcg cgcaaagtgc gctggcgcaa gggaatttca gccggcagga agccgcgcgc     180
atggcgcacc gtccgggtgt gatgcctcgt ggcggcccgc tcttcccgg gcggtcgctg     240 gccggggtgc cgggcttccc gctgcccagc attcatacgc agcaggcgta tgacccgcag     300
tcggacttta ccgcccgctg gacacgtgcc gacgcattgc agatcaaggc gcattcggat     360
gcgacggtcg cggccgggca gaattccctg ccggcgcaac tgaccatgcc gaacatcccg     420
gcggacttcc cggtgatcaa tccggatgtc tgggtctggg ataccctgga cctgatcgac     480
aagcacgccg atcagttcag ctataacggc tgggaagtca ttttctgcct gacggccgac     540
cccaatgccg atacggtttt cgacgaccgc acgtgcatg cccgcatcgg cttcttctat     600 cgtcgcgcg gtattcccgc cagcggcgg ccggtgaatg gcggctggac ctatggcggc     660
catctcttcc ccgacggagc cagcgcgcag gtctacgccg gcagacccta cacgaaccag     720
gcggaatggt ccggttcgtc gcgtctgatg cagatacatg gcaataccgt atcggtcttc     780
tataccgacg tggcgttcaa ccgtgacgcc aacgccaaca acatcacccc gccgcaggcc     840
atcatcaccc agaccctggg gcggatccac gccgacttca accatgtctg gttcacgggc     900
ttcaccgccc acacgccgct gctgcagccc gacggcgtgc tgtatcagaa cggtgcgcag     960
aacgaattct tcaatttccg cgatccgttc accttcgagg acccgaagca tcccggcgtg    1020
aactacatgt tgttcgaggg caataccgcg ggccagcgtg gcgtcgccaa ctgcaccgag    1080
gccgatctgg gcttccgccc gaacgatccc aatgcggaaa ccctgcagga agtcctggat    1140
```

```
agcggggcct attaccagaa ggccaatatc ggcctggcca tcgccacgga ttcgaccctg    1200
tcgaaatgga agttcctgtc gccgctgatt tcggccaact gcgtcaatga ccagaccgaa    1260
cggccgcagg tgtacctcca taacggaaaa tactatatct tcaccatcag ccaccgcacg    1320
accttcgcgg ccggtgtcga tggaccggac ggcgtctacg gcttcgtggg tgacggcatc    1380
cgcagtgact tccagccgat gaactatggc agcggcctga cgatgggcaa tccgaccgac    1440
ctcaacacgg cggcaggcac ggatttcgat cccagcccgg accagaaccc gcgggccttc    1500
cagtcctatt cgcactacgt catgccgggg ggactggttg aatcgttcat cgacacggtg    1560
gaaaaccgtc gcggggggtac cctggcgccc acggtccggg tgcgcatcgc ccagaacgcg    1620
tccgcggtcg acctgcggta cggcaatggc ggcctgggcg gctatggcga tattccggcc    1680
aaccgcgcgg acgtgaacat cgccggcttc atccaggatc tgttcggcca gcccacgtcg    1740
ggtctggcgg cgcaggcgtc caccaacaat gcccaggtgc tggcgcaggt tcgccaattc    1800
ctgaaccagt aa                                                       1812
```

```
<210> SEQ ID NO 14
<211> LENGTH: 20
<212> TYPE: DNA
<213> ORGANISM: Acetobacter
<220> FEATURE:
<223> OTHER INFORMATION: Primer

<400> SEQUENCE: 14
tgaaattgac gcccgttgga                                                 20

<210> SEQ ID NO 15
<211> LENGTH: 20
<212> TYPE: DNA
<213> ORGANISM: Acetobacter
<220> FEATURE:
<223> OTHER INFORMATION: Primer

<400> SEQUENCE: 15
cacgccggga aagaggattc                                                 20

<210> SEQ ID NO 16
<211> LENGTH: 20
<212> TYPE: DNA
<213> ORGANISM: Acetobacter
<220> FEATURE:
<223> OTHER INFORMATION: Primer

<400> SEQUENCE: 16
ggcaacgcgg tttctacgaa                                                 20

<210> SEQ ID NO 17
<211> LENGTH: 20
<212> TYPE: DNA
<213> ORGANISM: Acetobacter
<220> FEATURE:
<223> OTHER INFORMATION: Primer

<400> SEQUENCE: 17
cgttagccgg ggttgtcaga                                                 20

<210> SEQ ID NO 18
<211> LENGTH: 20
<212> TYPE: DNA
<213> ORGANISM: Acetobacter
<220> FEATURE:
<223> OTHER INFORMATION: Primer
```

<400> SEQUENCE: 18
tcgttgccac tttccgaggg                                              20

<210> SEQ ID NO 19
<211> LENGTH: 21
<212> TYPE: DNA
<213> ORGANISM: Acetobacter
<220> FEATURE:
<223> OTHER INFORMATION: Primer

<400> SEQUENCE: 19
gtcgattgtg tgcagcgtca a                                            21

<210> SEQ ID NO 20
<211> LENGTH: 20
<212> TYPE: DNA
<213> ORGANISM: Acetobacter
<220> FEATURE:
<223> OTHER INFORMATION: Primer

<400> SEQUENCE: 20
caccgatctt gtgcgtttcg                                              20

<210> SEQ ID NO 21
<211> LENGTH: 20
<212> TYPE: DNA
<213> ORGANISM: Acetobacter
<220> FEATURE:
<223> OTHER INFORMATION: Primer

<400> SEQUENCE: 21
cggcaatgct ccatcccac                                               20

<210> SEQ ID NO 22
<211> LENGTH: 20
<212> TYPE: DNA
<213> ORGANISM: Acetobacter
<220> FEATURE:
<223> OTHER INFORMATION: Primer

<400> SEQUENCE: 22
caccggaaag agtggcagga                                              20

<210> SEQ ID NO 23
<211> LENGTH: 20
<212> TYPE: DNA
<213> ORGANISM: Acetobacter
<220> FEATURE:
<223> OTHER INFORMATION: Primer

<400> SEQUENCE: 23
aaccgggtca cttgcgtcat                                              20

<210> SEQ ID NO 24
<211> LENGTH: 20
<212> TYPE: DNA
<213> ORGANISM: Acetobacter
<220> FEATURE:
<223> OTHER INFORMATION: Primer

<400> SEQUENCE: 24
agccatcgga gtcacatcgg                                              20

<210> SEQ ID NO 25

```
<211> LENGTH: 20
<212> TYPE: DNA
<213> ORGANISM: Acetobacter
<220> FEATURE:
<223> OTHER INFORMATION: Primer

<400> SEQUENCE: 25
ggaaacctcg aaaccctgcg                                              20

<210> SEQ ID NO 26
<211> LENGTH: 20
<212> TYPE: DNA
<213> ORGANISM: Acetobacter
<220> FEATURE:
<223> OTHER INFORMATION: Primer

<400> SEQUENCE: 26
tcagggcaat cactagccgg                                              20

<210> SEQ ID NO 27
<211> LENGTH: 20
<212> TYPE: DNA
<213> ORGANISM: Acetobacter
<220> FEATURE:
<223> OTHER INFORMATION: Primer

<400> SEQUENCE: 27
tcgagcagcc gtttcatcca                                              20

<210> SEQ ID NO 28
<211> LENGTH: 20
<212> TYPE: DNA
<213> ORGANISM: Acetobacter
<220> FEATURE:
<223> OTHER INFORMATION: Primer

<400> SEQUENCE: 28
tgatgcgctt gttcgtgacg                                              20

<210> SEQ ID NO 29
<211> LENGTH: 20
<212> TYPE: DNA
<213> ORGANISM: Acetobacter
<220> FEATURE:
<223> OTHER INFORMATION: Primer

<400> SEQUENCE: 29
cgttcgccct tgtcgtcatg                                              20

<210> SEQ ID NO 30
<211> LENGTH: 20
<212> TYPE: DNA
<213> ORGANISM: Acetobacter
<220> FEATURE:
<223> OTHER INFORMATION: Primer

<400> SEQUENCE: 30
gggccatccg ttacctgctt                                              20

<210> SEQ ID NO 31
<211> LENGTH: 20
<212> TYPE: DNA
<213> ORGANISM: Acetobacter
<220> FEATURE:
<223> OTHER INFORMATION: Primer

<400> SEQUENCE: 31
```
tgacacaccc gctccgaaat                    20

<210> SEQ ID NO 32
<211> LENGTH: 22
<212> TYPE: DNA
<213> ORGANISM: Acetobacter
<220> FEATURE:
<223> OTHER INFORMATION: Primer

<400> SEQUENCE: 32
gcatttgcgg taagtcatcc ca                 22

<210> SEQ ID NO 33
<211> LENGTH: 20
<212> TYPE: DNA
<213> ORGANISM: Acetobacter
<220> FEATURE:
<223> OTHER INFORMATION: Primer

<400> SEQUENCE: 33
ggatcccgat ttgcaagcca                    20

<210> SEQ ID NO 34
<211> LENGTH: 20
<212> TYPE: DNA
<213> ORGANISM: Acetobacter
<220> FEATURE:
<223> OTHER INFORMATION: Primer

<400> SEQUENCE: 34
tgtcgggtcg ggaactcaag                    20

<210> SEQ ID NO 35
<211> LENGTH: 20
<212> TYPE: DNA
<213> ORGANISM: Acetobacter
<220> FEATURE:
<223> OTHER INFORMATION: Primer

<400> SEQUENCE: 35
cgggttctcg ctgatgacct                    20

<210> SEQ ID NO 36
<211> LENGTH: 20
<212> TYPE: DNA
<213> ORGANISM: Acetobacter
<220> FEATURE:
<223> OTHER INFORMATION: Primer

<400> SEQUENCE: 36
tcccgcctgc atctgaagac                    20

<210> SEQ ID NO 37
<211> LENGTH: 20
<212> TYPE: DNA
<213> ORGANISM: Acetobacter
<220> FEATURE:
<223> OTHER INFORMATION: Primer

<400> SEQUENCE: 37
cagcgatgcc agccaatacc                    20

<210> SEQ ID NO 38
<211> LENGTH: 20
<212> TYPE: DNA

```
<213> ORGANISM: Acetobacter
<220> FEATURE:
<223> OTHER INFORMATION: Primer

<400> SEQUENCE: 38
gttcgtcgcg tctgatgcag                                              20

<210> SEQ ID NO 39
<211> LENGTH: 20
<212> TYPE: DNA
<213> ORGANISM: Acetobacter
<220> FEATURE:
<223> OTHER INFORMATION: Primer

<400> SEQUENCE: 39
acctgggcat tgttggtgga                                              20

<210> SEQ ID NO 40
<211> LENGTH: 22
<212> TYPE: DNA
<213> ORGANISM: Acetobacter
<220> FEATURE:
<223> OTHER INFORMATION: Primer

<400> SEQUENCE: 40
ctcaggaaga ccgaattgat ta                                           22

<210> SEQ ID NO 41
<211> LENGTH: 19
<212> TYPE: DNA
<213> ORGANISM: Acetobacter
<220> FEATURE:
<223> OTHER INFORMATION: Primer

<400> SEQUENCE: 41
gcgaaacgtc tgattgaac                                               19

<210> SEQ ID NO 42
<211> LENGTH: 38
<212> TYPE: DNA
<213> ORGANISM: Acetobacter
<220> FEATURE:
<223> OTHER INFORMATION: Primer

<400> SEQUENCE: 42
cggataacca ctggtgctcc gactcgcctc actctact                          38

<210> SEQ ID NO 43
<211> LENGTH: 39
<212> TYPE: DNA
<213> ORGANISM: Acetobacter
<220> FEATURE:
<223> OTHER INFORMATION: Primer

<400> SEQUENCE: 43
tccacgaatc tcacgaagca ccccgacctt atctcccat                         39

<210> SEQ ID NO 44
<211> LENGTH: 22
<212> TYPE: DNA
<213> ORGANISM: Acetobacter
<220> FEATURE:
<223> OTHER INFORMATION: Primer

<400> SEQUENCE: 44
gccaggcgtg tacatataac ta                                           22
```

```
<210> SEQ ID NO 45
<211> LENGTH: 22
<212> TYPE: DNA
<213> ORGANISM: Acetobacter
<220> FEATURE:
<223> OTHER INFORMATION: Primer

<400> SEQUENCE: 45
cggaatacct agttggaaca ct                                              22

<210> SEQ ID NO 46
<211> LENGTH: 21
<212> TYPE: DNA
<213> ORGANISM: Acetobacter
<220> FEATURE:
<223> OTHER INFORMATION: Primer

<400> SEQUENCE: 46
tcaagatcga tgcacctatt c                                               21

<210> SEQ ID NO 47
<211> LENGTH: 20
<212> TYPE: DNA
<213> ORGANISM: Acetobacter
<220> FEATURE:
<223> OTHER INFORMATION: Primer

<400> SEQUENCE: 47
aacagacagt tctggtagga                                                 20

<210> SEQ ID NO 48
<211> LENGTH: 37
<212> TYPE: DNA
<213> ORGANISM: Acetobacter
<220> FEATURE:
<223> OTHER INFORMATION: Primer

<400> SEQUENCE: 48
cgcatctcca gatcggcagg tcgtccagtc gatcatg                              37

<210> SEQ ID NO 49
<211> LENGTH: 38
<212> TYPE: DNA
<213> ORGANISM: Acetobacter
<220> FEATURE:
<223> OTHER INFORMATION: Primer

<400> SEQUENCE: 49
acatctgtcc acggcattgg tggctggctt atgagtct                             38

<210> SEQ ID NO 50
<211> LENGTH: 19
<212> TYPE: DNA
<213> ORGANISM: Acetobacter
<220> FEATURE:
<223> OTHER INFORMATION: Primer

<400> SEQUENCE: 50
gagaagtcct ctgcttcgg                                                  19

<210> SEQ ID NO 51
<211> LENGTH: 18
<212> TYPE: DNA
<213> ORGANISM: Acetobacter
<220> FEATURE:
```

<223> OTHER INFORMATION: Primer

<400> SEQUENCE: 51
cggcggttga gaagatgt                                                        18

<210> SEQ ID NO 52
<211> LENGTH: 19
<212> TYPE: DNA
<213> ORGANISM: Acetobacter
<220> FEATURE:
<223> OTHER INFORMATION: Primer

<400> SEQUENCE: 52
ggaagacatc aacgaagca                                                       19

<210> SEQ ID NO 53
<211> LENGTH: 19
<212> TYPE: DNA
<213> ORGANISM: Acetobacter
<220> FEATURE:
<223> OTHER INFORMATION: Primer

<400> SEQUENCE: 53
ttgacagttg catagtccg                                                       19

<210> SEQ ID NO 54
<211> LENGTH: 39
<212> TYPE: DNA
<213> ORGANISM: Acetobacter
<220> FEATURE:
<223> OTHER INFORMATION: Primer

<400> SEQUENCE: 54
atacggctcg tcatgtcgcg gtgatggata atctcagcc                                 39

<210> SEQ ID NO 55
<211> LENGTH: 40
<212> TYPE: DNA
<213> ORGANISM: Acetobacter
<220> FEATURE:
<223> OTHER INFORMATION: Primer

<400> SEQUENCE: 55
cagtggccga acctggaagc gctgatataa gcctgaagat                                40

<210> SEQ ID NO 56
<211> LENGTH: 17
<212> TYPE: DNA
<213> ORGANISM: Acetobacter
<220> FEATURE:
<223> OTHER INFORMATION: Primer

<400> SEQUENCE: 56
attgcaccgc gttgatg                                                         17

<210> SEQ ID NO 57
<211> LENGTH: 18
<212> TYPE: DNA
<213> ORGANISM: Acetobacter
<220> FEATURE:
<223> OTHER INFORMATION: Primer

<400> SEQUENCE: 57
gcgtaacggt cacaagga                                                        18

```
<210> SEQ ID NO 58
<211> LENGTH: 22
<212> TYPE: DNA
<213> ORGANISM: Acetobacter
<220> FEATURE:
<223> OTHER INFORMATION: Primer

<400> SEQUENCE: 58
aggaggctct tctttggaa gc                                             22

<210> SEQ ID NO 59
<211> LENGTH: 22
<212> TYPE: DNA
<213> ORGANISM: Acetobacter
<220> FEATURE:
<223> OTHER INFORMATION: Primer

<400> SEQUENCE: 59
aagtgcccct gttatcgtac ac                                            22

<210> SEQ ID NO 60
<211> LENGTH: 22
<212> TYPE: DNA
<213> ORGANISM: Acetobacter
<220> FEATURE:
<223> OTHER INFORMATION: Primer

<400> SEQUENCE: 60
tgggtcatcg gttctgattt cc                                            22

<210> SEQ ID NO 61
<211> LENGTH: 22
<212> TYPE: DNA
<213> ORGANISM: Acetobacter
<220> FEATURE:
<223> OTHER INFORMATION: Primer

<400> SEQUENCE: 61
tagtttgatg tcgggtgctg ag                                            22

<210> SEQ ID NO 62
<211> LENGTH: 22
<212> TYPE: DNA
<213> ORGANISM: Acetobacter
<220> FEATURE:
<223> OTHER INFORMATION: Primer

<400> SEQUENCE: 62
gcgaataccg gtcttttac gc                                             22

<210> SEQ ID NO 63
<211> LENGTH: 21
<212> TYPE: DNA
<213> ORGANISM: Acetobacter
<220> FEATURE:
<223> OTHER INFORMATION: Primer

<400> SEQUENCE: 63
atgcaagctc cggattgaga g                                             21

<210> SEQ ID NO 64
<211> LENGTH: 20
<212> TYPE: DNA
<213> ORGANISM: Acetobacter
<220> FEATURE:
<223> OTHER INFORMATION: Primer
```

<400> SEQUENCE: 64
ccaaatctct ggaacgggta                                              20

<210> SEQ ID NO 65
<211> LENGTH: 420
<212> TYPE: DNA
<213> ORGANISM: Acetobacter
<220> FEATURE:
<223> OTHER INFORMATION: hypothetical protein coding sequence

<400> SEQUENCE: 65
atgcggatca gcggcatatc ttcgattctc gataatgcaa cggcccagtc ctcatcgggt     60
gccacgacac agaagagcgg gattttgcaa tcatcgtctc tcgatttcag caatatttcc    120
gcgtcgaatc tgcaagacgt gaatgcggaa ctctataatc aggggaagat atcgctccgt    180
cagagcggtg acttgtcctt gttggatggg tgggcactca agggcgtcaa taatggtcaa    240
cttcggcagt catcgaccgg aaccctcaac gcctattcct tgcttgatac catgattaat    300
tatcaggaaa cgaacggtat cggcgatgta aagatacgg tcgcatccct caaggcattg     360
cgcagtacac ttgaggaata tgataccaac aatcagaata aaacggcgat cacggcctaa    420

<210> SEQ ID NO 66
<211> LENGTH: 864
<212> TYPE: DNA
<213> ORGANISM: Acetobacter
<220> FEATURE:
<223> OTHER INFORMATION: GDIA_RS17945 (7136..7999)- hypothetical protein

<400> SEQUENCE: 66
atgtacgttt cagtggcaaa ggctggtacc atcgttgata gcctgtcgac gagggagaag     60
agcaaagagg gaggcggcac gctcctgacg tccgatcagc cagattccgc tgaaacaggc    120
cacgccgaga ccgaatctgt ttcgattacg ctgtctcagg cggccgtcga cgctttgaac    180
gggactgcct cgcagaacac tccggcttcc atgcaactcg ccatgtcccg catgaccag     240 attatccggt ccggcaacag cgcggcaaaa gccgatgccg gggcgcgtgt cgccaatttg    300
caggcgcaga tgcggcagct catggagacc aaggatctca tgtcgccaaa agcgctggcg    360
gccgccctgg cgctgatggc ccgcgaactg gccgccgccg tcagcgagta tgtgcaatgc    420
ggcggatcgg ctgccaacgc ggccattggt accgtcgtac tatccgcgtc ggccgacaca    480
tcggctgatc cgtccactgc cgccccggca acatctgtaa cggcggatca acccgttgcg    540
tcggttcccc aggacgcgac acaggaacag agtgcccaag gccagaccgc tcccgggcag    600
agcggtcagc agacccagga aggaaacgcc gtcgatcatt cgagcgatga gacggaacag    660
accgcaggtg cggcaaatac ccagcctaaa gaaagcgggg acgacctgtt tgccaaggcc    720
gtgaagagcc tggcggagga aatgaagagc atcctcaacg aactgaagaa caagaagaaa    780
aaggacgatg cgtccgaaga ccatgatctt caatcgacac agggttctct cgacagaatc    840
gatcagatga ttggaggcat ataa                                          864

<210> SEQ ID NO 67
<211> LENGTH: 1392
<212> TYPE: DNA
<213> ORGANISM: Acetobacter
<220> FEATURE:
<223> OTHER INFORMATION: GDIA_RS17965 (13228..14619)- HlyD family type I
      secretion periplasmic adaptor subunit

<400> SEQUENCE: 67

```
tcatggctcc ctcataccgt cagtcatgag cggaatgaga ttgttaagaa gaaattgcat    60
aatggttcgt gtacccactt gaatatctgc tgtaatgggc attcctgcc gggggtgaaa    120 cgatgaaggt acgccgtgca accgataatc ttcgatatgc agccgtgcgc gataatagga   180
ctgtgccgca gcggcaggat cgttgctcgc tcgctgcccg atcccgccgt ttgatacggc   240
gtcctgtgac gtattaccat cgaacgtgtc tgcgctgatt tctcgtacca gcgcctcagc   300
accgccatac tgagagtatg gaaatgccgc gaacttgata attgccttgt tgccgggttg   360
cacaaaaccc gcatctttgc tgcttaaatg cacctcgact tcaagaccgc tatcgactgg   420
aacaagccgc atcagctctg ccccggttgt cagaacggac ccaggtgaca atctggcgat   480
cgtcaggacg actgcatcct cttgcgccgt caagatggtc atgcttttgc ggagcttcgc   540
cttttgatag tcggcatccg tggttgagag cttgtgttgt gcctcgctta aatcgcgata   600
gatgtccgct ctccatgttt caatatattc ttggcgttcg gcgacgagcg cctgcaactt   660
ggcttttgcc gatgctgcgt catgctgggc aaggacctcg gagcgctgaa cttccatcat   720
atcgttctga gcgccaagag tagaaaggcg gctgcccacc tgttcctcct gcaagcgagt   780
tcgcatcctg tgtacgttgg tcgcgacttc gagccgttta gcgtagatgg tagcgttggc   840
cagcgcgcct tggagatcgg ccgcctggga agccagttgt tcttgatagt tctcgatttt   900
ggccgcaaac tcagccttac gacgcaggaa tgtcgccgct tgctgtattg acgctgggtc   960 gtcgggtcc gacaggtagt ccctaccctg cgcttccgca gaaaggcgtg cgacttccgc   1020
agtataactt tgggtttgtg acttcaaatt tgcgatatca gcgtcgttaa ccgtagggtc   1080
aaggcgggat aatacttggc ccttatgaac aaggtcacct ccccgcacgt ccacactacg   1140
aataatcgac gtttcgaacg gctgtacaac gagaggtctc tgaatagata ctattttccc   1200
ttcggtggac accacccgag tcagcggaaa gaccatcatg aatacgatac tactcgcggt   1260
cagcgcacca attatccaag atatatagcg ggctgaaggc gtggccggca tgttgacaag   1320
cgcggcagtc ggcgaatgaa actcaagcaa cgccggaggc aaatcggcat agtcaaagga   1380
gtcagtctcc ac                                                       1392
```

<210> SEQ ID NO 68
<211> LENGTH: 849
<212> TYPE: DNA
<213> ORGANISM: Acetobacter
<220> FEATURE:
<223> OTHER INFORMATION: GDIA_RS18030 (25282..26130) - hypothetical
      protein

<400> SEQUENCE: 68

```
tcaagatttt ttaccttccc gctcgattgt gacggaagcg gcgagttcct tgatcgcggc    60
gacgctggca tcggctcgtt cctcagcccg gatggcgcgg gcttccgctg cctgcacgcg   120
ggattccgca cgggcttcgg ccgcgtcacg ggacttttca gcgttctcca gtgccgtggc   180
agcggtgctg gcccgacgct ccgcgatgtc ctgggctttc tccgccgcct gggcacgggc   240
ctgggcctcg gacacggcct gccgcagggc gtcgatctcc ccggtctgcc gctcggccat   300
ggcacgcgcc gcctgatggg cctgacgttc agcggtcagt tcgaccgtca gccggtccac   360
ctcccgctgc aaggcctcca gccggcgtgt cagcccttca gcctcggccg tagcgccagc   420
cagggcttcc gccaattcca tcgcctcccc cctggcatcg gcagctccg cacccgcctg   480 agcctggata tcgcgatct ctggtccgc gcttcccgc ccagcgcca ccttctggtc    540 ggccgccgcc tggatggcct gctggacgga ttgccctttc tggcgctccg catcgacaaa   600
```

```
gccggtcagc atcgccagga agccctgctt catccgttcg gccgcgttgt ccatctcggc    660
cgagacgaga tccccggctt cgctccgggg ctcctccttc ggtgcttcga ccggccgccc    720
gcgctgactg tctttccagg cgttgagcag cggcaggatg gcgttcggac tgccgccccc    780
cagctcgtcc cgcactttgc gcacactggg cttctcgccc cgcccgacca gcgcttcggc    840
ggcctgcat                                                           849
```

MICROORGANISMS AND THEIR USE IN AGRICULTURE

The present invention relates to novel microorganisms, specifically novel strains of the nitrogen-fixing bacteria *Gluconacetobacter diazotrophicus* (Gd), and their use in agriculture, including agriculturally acceptable compositions containing these microorganisms. The strains have good utility in agriculture, in terms of their ability to colonise plant cells intracellularly, giving rise to particularly effective nitrogen fixation. Kits for identification and monitoring of the use of these strains form the subject of a co-pending application.

BACKGROUND OF THE INVENTION

*Gluconacetobacter diazotrophicus* (Gd) has been well studied for its nitrogen fixing and plant growth promoting activities as reviewed in Eskin et al. International Journal of Agronomy (2014):1-13. Certain strains of Gd however have been shown to be particularly advantageous in the treatment of plants since they are able to establish themselves intracellularly within plant cells along with exhibiting species and tissue independence (Cocking et al., In vitro Cellular & Developmental Biology Plant (2006) 42 (1). These properties, combined with their ability to travel throughout a range of plant tissues, make such strains better able to deliver the benefits to the target crop plants.

However, a wide range of strains of Gd exist and it has not yet been possible to provide a means for easily identifying strains which have these beneficial properties.

Furthermore, an important aspect of bio-fertiliser has been to provide an alternative to the chemical fertilisers in a nature friendly way to agricultural crop plants. However, it would be helpful to validate the effectiveness of any on-going treatment in field conditions, so that a farmer is able to determine what levels of nitrogen fertiliser, if any, are required to be supplied to enhance growth conditions.

The applicants have found specific advantageous strains of Gd contain a number of unique nucleic acid sequences that are not found in other Gd species, nor in any other species, including plant species. This means that the beneficial strain can be readily identified and gives rise to the provision of a reliable diagnostic test, useful in both monitoring of treatments in the fields and in research, for identifying related beneficial strains.

SUMMARY OF THE INVENTION

According to the present invention, there is provided a strain of *Gluconacetobacter diazotrophicus* (Gd) characterised by the presence of at least one nucleic acid sequence selected from SEQ ID NOS 1-10 or variants or paralogues thereof and/or the presence of a single plasmid of about 17566 bp in size.

Strains having these unique characteristics have been found to be particularly effective in intracellular colonization of plant cells resulting in beneficial nitrogen fixing. In particular, it has been found that use of a stain of the invention leads to yield enhancements in crops such as cereal crops like maize and wheat. Alternatively, similar yields can be achieved even with reduction in traditional nitrogen fertiliser applications.

Sequences of SEQ ID NO 1-10 (shown in attached Table 1) hereinafter, are present in the particular strain IMI504853 but do not appear in genomic analyses of other available strains.

Variants of SEQ ID NOs 1-10 will include allelic forms which are highly naturally occurring variants. They will have a high level of sequence identity, for example, at least 70%, 70%, for instance at least 71%, 75%, 79%, 81%, 84%, 87%, 90%, 93%, 95%, 96% or 98% identical to the basic sequence. Identity in this context may be determined using the BLASTP computer program with SEQ ID NO 2 or a fragment, in particular a fragment as described below, as the base sequence. The BLAST software is publicly available at blast.ncbi.nlm.nih.gov (accessible on 27 Jul. 2015).

In particular however the strain of the invention is characterized by the presence of at least one nucleic acid of SEQ ID NOS 1-10, suitably at least 3 different nucleic acid sequences of SEQ ID NOS 1-10, for example at least 5 or at least 8 different nucleic acid sequences of SEQ ID NOS 1-10, and in particular by the presence of all nucleic acid sequences of SEQ ID NOS 1-10.

Preferred strains may also be characterised by the presence of a single plasmid of about 17566 bp in size. The presence of a plasmid, in particular of this size, differs from a previously known strain of Gd, UAP5541, which has been reported as lacking in plasmids (Luis E. Fuentes-Ramièrez et al., FEMS Microbiology Ecology 29 (1999) 117-128). Furthermore, the size of the plasmid is smaller than that reported previously in respect of PAL5 strains containing a single plasmid (Giongo et al. Standards in Genomic Sciences, May 2010, Volume 2, Issue 3, pp 309-317 doi: 10.4056/sigs.972221).

The plasmid of strains of the invention may also be characterized in that it is restricted into two fragments by the restriction enzyme EcoRI, wherein the fragments are about 12 Kb and about 5.6 kb in size respectively. Furthermore, the plasmid lacks a number of key sequences which have been previously identified as being present in the plasmid of PAL5. These sequences are shown as SEQ ID Nos 65, 66, 67 and 68 in the attached sequence listing. Thus the absence of these particular sequences may provide a further characterizing feature of the strains of the invention.

A strain of the invention has been deposited with CABI in the UK under the Budapest Treaty with deposit accession number IMI 504958 (formerly IMI 504853).

Dot plot analysis of the plasmid of this strain was performed against the small plasmid (NC_010123; 16610 bp) from PalS DNA sequence analysis (M. Bertalan et al. BMC Genomics (2009) 10:450 DOI: 10.1186/1471-2164-10-450) using GEPARD software V 1.30 (Krusiek et al. Bioinformatics 2007; 23(8): 1026-8). Interestingly, no plot was produced when DNA sequences of the two plasmids were compared. This indicates that the homology is so low that no structural similarity could be established by the software; thus confirming that the plasmid is a single and unique plasmid.

For use in agriculture, the strains of the invention are suitably formulated into an agricultural composition.

Thus a further aspect of the invention comprises an agricultural composition comprising a strain as described above in combination with an agriculturally acceptable carrier. Generally the concentration of nitrogen-fixing bacteria that is present in the composition will vary depending upon factors such as the manner of administration, the type of plant or seed being treated and the particular strain of Gd used and the level of enhanced nitrogen-fixation required. Typically however, the compositions will comprise a solution containing from 1 to $1\times10^9$ bacteria per millilitre of composition, for example from $10\text{-}10^3$ bacteria per millilitre of composition for instance from 50-200 bacteria per millilitre of composition such as 100 bacteria per millilitre of composition. Such a composition may be obtained by culturing the bacteria to a readily detectable level for example by examining the optical density and then diluting the solution accordingly.

The Gd may be the sole active component of the composition or it may be combined with additional agrochemically active components such as insecticides, fungicides or plant growth regulators, provided these are compatible with Gd.

The composition of the invention suitably comprises a solvent such as water although organic solvents, such as vegetable oils or hydrocarbons such as paraffin or kerosene oils may be used if required. Suitably any organic solvent is a vegetable oil such as soybean oil, sunflower oil, canola oil (oilseed rape oil), cottonseed oil, castor oil, linseed oil or palm oil or mixtures of these.

The composition may further comprise additives or excipients such as thickening agents, dispersants, diluents, humectants, solid carriers etc. as are known in the art.

In a particular embodiment, the composition further comprises a polysaccharide or an agriculturally acceptable surfactant or a combination of these. The applicants have found that such components may enhance the activity of the composition, as described in a co-pending British patent application. Suitable polysaccharides include hydrocolloid polysaccharides derived from plant, animal or microbial sources.

In particular, these include exudate gum polysaccharides such as gum Arabic, gum ghatti, gum karaya and gum tragacanth, cellulosic derivatives such as carboxymethylcellulose, methylcellulose, hydroxypropyl cellulose, hydroxypropyl methylcellulose or microcrystalline cellulose, starches and derivatives including, for instance corn starch, tapioca starch, potato starch, rice starch, wheat starch, and modified versions thereof such as pregelatinized starch, oxidized starch, ethylated starch, starch dextrins or maltodextrin, pectin, polysaccharides derived from seaweed such as agar, alginates, carrageenan, and fucellaran, seed gums such as guar gum and locust bean gum, polysaccharides derived from microbial fermentation such as xanthan gum and gellan gum, and nitrogen containing polysaccharides such as chitosan; or mixture of these.

In a particular embodiment, the polysaccharide is exudate gum polysaccharide such as gum Arabic, gum ghatti, gum karaya or gum tragacanth. A particular example of the polysaccharide is gum Arabic.

The amount of polysaccharide present in the composition may vary depending upon factors such as the manner of administration, the type of plant or seed being treated and the particular strain of Gd used and the level of enhanced nitrogen-fixation required. This will vary depending upon the various factors such as the particular polysaccharide used, the type of plant or seed being treated, the particular strain of nitrogen-fixing bacteria employed and the method of administration. However, typically, a composition comprising from 0.1 to 1% w/w, for example from 0.1 to 0.5% w/w such as about 0.3% w/w polysaccharide is used.

In a particular embodiment, the composition further comprises a surfactant or detergent including in particular a non-ionic detergent such as those sold under the trade name 'Tween'®, for example Tween 80. Tween 80 is a non-ionic detergent; 70% composed of the fatty acid oleic acid and the remainder a combination of linoleic, palmitic and stearic acids. The pH of a 1% solution is in the range of from 5.5-7.2. It is widely used for emulsifying and dispersing substances in medicinal and food products. It has little or no activity as an anti-bacterial agent (Dawson et al. (1986) Data for Biochemical Research, 3rd ed., Oxford University Press (New York, N.Y.: 1986), p. 289). The amount of surfactant included vary depending upon the various factors such as the particular surfactant used, the type of seed being treated, the manner of administration, the type of plant or seed being treated and the particular strain of Gd used and the level of enhanced nitrogen-fixation required. However, typically, a composition comprising from 0.0005 to 0.2% v/v for example from 0.0005 to 0.15% v/v such as about 0.001% v/v.

Suitably a nutrient for the Gd is also included in the composition. Examples include a 3% w/v sucrose solution as described in EP-B-1422997.

Since by and large, all the components of the compositions are natural products, the environmental impact of the treatments of the invention is low and the compositions may satisfy regulatory requirements relatively easily.

In a particular embodiment, the formulation is applied as a seed coating as described above. In particular, the formulation is applied to seeds, either by spraying or by soaking and the seeds are then dried to form a residual coating comprising Gd thereon.

A further aspect of the invention provides a method for enhancing the nitrogen-fixing ability of a plant, said method comprising administering to the plant or to the environment thereof, a strain of Gd as described above, or an agricultural composition comprising it so that the Gd colonises plants and in particular enters plant cells (intracellular colonisation).

This may be achieved in a variety of ways. For example, the Gd may be administered to a growth medium of the plant, in particular on or after germination, using a method as described for example in EP-A-1714545. In this case, administration of in particular low levels for example from 1-100 bacteria per millilitre of inoculum to the growth media such as agar is applied to grasses, in for example on germination or shortly thereafter, for example up to 7 days thereafter.

Alternatively, the Gd may be applied to a seed in particular to the surface of a seed, for example in a pre-germination soak or, in a particular embodiment, as a seed coating. Alternatively, the one or more compositions may be applied to a growth medium on which the seeds are allowed to germinate. Such growth media include artificial media such as agar gels as well as soils or composts in which the seeds are about to be or have been sown.

In yet another embodiment, the Gd is applied to growing plants in and particular to a wound of the plant. This technique is described in the applicants copending International Patent Application No PCT/GB2015/052170. In this method, the nitrogen-fixing bacteria is administered to a wound of a growing plant. The wound may be a result of accidental or natural damage, whereupon the additional nitrogen availability may facilitate repair growth. However, in a particular embodiment, the wound is the result of damage caused by actions such as mowing (amenity grass), cutting (silage and hay crops), consumption by livestock (pasture grass) or by harvesting. Therefore, a preliminary step of inflicting 'damage' on the grass, in particular by mowing, cutting, or by harvesting may be carried out before administration of the nitrogen-fixing bacteria. The nitrogen-fixing bacteria is suitably applied within a relatively short time period of carrying out such actions, for instance, within 48 hours, for instance within 24 hours, such as within 10 hours and suitably within 1-2 hours of damage being inflicted on the plant.

Delivery of the bacteria is achieved by application of a suitable formulation to the wound area in particular in the form of a composition. The composition may be in the form of a liquid, gel, paste which may be applied directly or in diluted form, or it may be in the form of a solid composition such as a powder or granule composition that will be dissolved in liquid such as water before use. In solid compositions, the bacteria will generally be used in dried form, for example in freeze-dried form, which are reconstitutable on addition of water. However, the desiccation resistance of the present strains may mean that freeze-drying is not required.

In a particular embodiment, the composition is in a form suitable for spraying on the plants and thus will comprise a concentrate for dilution which may be in the form of a liquid or solid, in particular in the form of a liquid, or it may comprise a dilute aqueous composition that may be sprayed directly.

The amount of nitrogen-fixing bacteria that is administered in any particular case will vary depending upon factors such as the type of seed or plant being treated, the particular strain of nitrogen-fixing bacteria used, the level of germination enhancement required and the method of administration. Typically however, the seeds or the environment thereof such as the growth medium is inoculated with a solution containing from 1 to $1 \times 10^9$ bacteria per millilitre of inoculum, for example from 1-100 bacteria per millilitre of inoculum, for instance from 10-80 bacteria per millilitre of inoculum such as 50 bacteria per millilitre of inoculum. Such a solution may be obtained by culturing the bacteria to a readily detectable level for example by examining the optical density and then diluting the solution accordingly.

In a particular embodiment, the Gd is administered together or in combination with a strain of *Terribacillus*, as described in the applicants co-pending International patent application No. PCT/GB2015/052171. The applicants have found that such a strain may enhance the activity of the Gd. Suitable strains of *Terribacillus* include *Terribacillus saccharophilus*, *Terribacillus halophilus*, *Terribacillus goriensis* or *Terribacillus aidingensis* but in particular is a strain of *Terribacillus saccharophilus*. The *Terribacillus* is administered either separately or in admixture with the Gd. The *Terribacillus* may be in intimate admixture with the Gd, or it may be administered in a co-culture, or mixed culture form.

Suitable plants include leguminous and non-leguminous crops and ornamentals. The non-leguminous plant is preferably selected from the grass family Gramineae (includes rice [*Oryza sativa*], wheat [*Triticum aestivum*] and maize [*Zea mays*]). The non-leguminous plant may also be one selected from families such as: Solanaceae (includes tomato, potato and tobacco), Brassicaceae/Cruciferae (includes cabbages, turnips, oilseed rape and the model plant *Arabidopsis thaliana*), Malvaceae (includes cotton), Compositae/Asteraceae (includes sunflower and lettuce), Euphorbiaceae (includes cassava), Chenopodiaceae (includes sugar beet). The leguminous plant is preferably selected from the Leguminosae (includes soybean, clover, alfalfa, peas and other beans). Seeds treated may be of monocotylendous or dicotylenous plants but in particular are monocotylendous plants such as grasses, rice, wheat, barley, sorghum, millet, oats, rye and maize. In particular the seeds treated in accordance with the method of the invention are grasses such as *Lolium perenne*.

Other crops listed above may use the Gd to facilitate survival in non-optimal pH conditions as described above.

Once inoculated as described above, the Gd of the invention will colonise the plant cells and act symbiotically within the plant to enhance nitrogen-fixation.

Thus a further aspect of the invention provides a plant or seed which has been colonised by a strain of Gd as described above. In particular the Gd is located intracellularly in living plant cells.

The applicants have found that intracellular Gd will pass from generation to generation and that thus seeds and other progeny obtained from the seeds and plants of the invention will also comprise intracellular Gd. Such seed or progeny form yet a further aspect of the invention.

By enhancing nitrogen-fixation, plants may show enhanced properties, such as more rapid or improved growth characteristics and/or improved yield. In a further aspect, the invention provides a method for producing a plant product, said method comprising growing a plant colonised with Gd as described above, and obtaining the product therefrom.

In addition, the applicants have noted that certain plants colonised by nitrogen-fixing bacteria, in particular intracellularly colonised plants, show not only enhanced growth or yield characteristics, but also show an increased chlorophyll level as compared to plants without such intracellular bacteria. The plants which appear particularly to demonstrate this property are grasses including pasture, amenity or turf grasses. This is particularly advantageous in the context of such plants as high chlorophyll levels give rise to a better green colouration, which is highly desirable in an ornamental context.

Thus, in a further aspect, the invention provides a method for increasing chlorophyll in grasses, which method comprises growing grasses which comprise Gd as described above.

The grasses may include grasses such as pasture, amenity, turf or ornamental grasses, for example, *Lolium* spp, such as *Lolium perenne*, *Lolium multiflorum*, *Lolium persicium*, *Agrostis* spp. such as *Agrostis castellana*, *Agrostis capillaris*, *Agrostis stoloniferia*, *Festuca* spp such as *Festuca rubra*, *Festuca ovina*, *Festuca longifolia*, *Festuca arundinacea*, *Poa* spp such as *Poa annua*, *Poa Pratensis* and *Poa trivialis*, *Paspalum vaginatum*, *Cynodon* spp such as *Cynodon dactylon*, *Zoysia* spp such as *Zoysia japonica*, *Zoysia tenuifolia*, or *Emerald Zoysia*, *Stenotaphrum secundatum*, *Buchloe dactyloides* or *Pennisetum clandesinium*. Generally however, *Lolium* spp. and/or *Festuca* spp. form the basis of many amenity or turf grasses.

The Gd may be administered to the grasses using any of the techniques described above, but in particular, may be applied to the seeds of the grasses as a coating, or to wounds of the grass, inflicted after cutting.

Strains in accordance with the invention may be identified and/or monitored by use of a diagnostic kit comprising means to determine the presence in a sample of at least one nucleic acid sequence selected from SEQ ID NOS 1-10.

As discussed above, SEQ ID NOs 1-10 represent unique and novel sequences, which appear in a preferred subspecies or strain of Gd. Thus they provide a means for identifying these beneficial strains. In addition, they have been found to be amenable to detection using primers which do not cross-react with plant species.

Furthermore, since the strains can colonise intracellularly in the host plant cells, they are able to effectively travel throughout the plant. The kit of the invention can be used to provide an evaluation of colonisation by Gd post-germination at a young stage and check its efficiency. This will then allow the farmers to make an "informed decision" about the existence and extent of the colonisation and if required how much chemical based nitrogen fertiliser will be required to be applied. This extra level of security will provide 'assurance' to farmers that their crops are being well-tended, even when using nature and crop friendly fertiliser in the form of Gd.

In a particular embodiment, the kit may comprise means for determining the presence of more than one of the nucleic acid sequences of SEQ ID NOs 1-10, for example up to 10, such as up to 5, or up to 3 of said nucleic acid sequences of SEQ ID NOs 1-10. In this way, a reliable diagnostic kit would be provided which will ensure that the strain detected is the one which is similar or substantially similar to the beneficial strain. Similar strains would be detected even if one or more of the sequences differs for example as result of mutation.

Preferred strains appear to contain a plasmid, and so plasmid detection, for example by isolation using a commercially-available plasmid isolation kit, may provide further confirmation of the identification of a beneficial strain. In particular, any plasmid identified should be less than 27455 bp in size, for example about 17566 bp. The presence of a plasmid, in particular of this size, differs from a previously known strain of Gd, UAP5541, which has been reported as lacking in plasmids (Luis E. Fuentes-Ramièrez et al., FEMS Microbiology Ecology 29 (1999) 117-128). Furthermore, the size of the plasmid is smaller than that reported previously in respect of PAL5 strains containing a single plasmid.

The plasmid may be subject to cutting, in particular by means of an EcoRI restriction enzyme, to yield two fragments of about 12 kb and about 5.6 kb.

The diagnostic kit may further comprise means for determining the presence of at least one nucleic acid sequence which is characteristic of Gd species, for example 2, or 3 nucleic acid sequences which are characteristic of Gd species. In this way, the kit would provide confirmation that some Gd is present in the sample, thus confirming the accuracy of the test. If the sample is known to contain Gd, a positive result in this determination would act as a 'control' confirming that the test has been carried out effectively. Suitable specific strains will be sequences found in Gd species generally but not in other species, and in particular not in other microbial species or in at least some plants, in particular plants which may be targeted for Gd treatments.

Particular examples of such sequences are shown as SEQ ID NOS 11-13 in Table 2 hereinafter. In particular, these nucleic acid sequence which is used to detect Gd species have been found to be amendable to detection of Gd species present in a range of crops, without cross-reacting with plant species.

In addition, the kit may comprise means for detecting sequences which are not found in the strain of the invention, to provide a negative control. Examples of such sequences are shown as SEQ ID Nos 65-68. In a further embodiment, the kit comprises means for detecting the presence of a plant specific nucleic acid sequence, such as a chloroplast specific nucleic acid which amplifies universally from plant DNA. The inclusion of such means will act as a control when the kit is used in the context of detection of Gd within a plant species, as this means will produce a detectable signal, even in the absence of any Gd. If this signal fails, this would indicate failure in the test rather than necessarily that there is no Gd present. A particular chloroplast primer set which is available commercially from Thermo Scientific. Product as Phire Plant Direct PCR Master Mix, is based on the disclosure by Demesure B et al (1995) Molecular Ecology 4:129-131.

The means for detecting the presence of the nucleic acid sequences may take various forms as would be understood in the art.

Where the nucleic acids are genes which are expressed, the kit may comprise means for detecting the expressed proteins. Such means may include specific protein tests such as immunochemical analysis which utilise antibodies specific to the proteins to immobilise and/or detect the proteins, such as ELISA or RIA techniques, or immunoelectrophoretic methods such as Western blotting.

However, in a particular preferred embodiment, the kit of the invention comprises means for detecting specific nucleic acids themselves.

In particular, nucleic acids may be detected using any of the available techniques including nucleic acid binding assays and immunoassays using antibodies raised to haptenised forms of the nucleic acids. However, in a particular embodiment, the detection involves nucleic acid amplification reactions, and thus in particular, the kits will comprise one or more amplification primers which target the or each nucleic acid sequence being detected.

As would be understood by a skilled person, when detection of a sequence is carried out using an amplification reaction, it would not be necessary to amplify the entire sequence, but rather just a characteristic fragment of the entire sequence, for example a fragment of at least 10, and suitably at least 50 base pairs. Thus the size of the sequence that may be amplified would could be in the range of from 10-3070 base pairs, and suitably from 20-2000 base pairs, for example from 50-500 base pairs, such as from 100-300 base pairs. The size of the fragment will depend upon the nature of the detection reaction being used, but it should be sufficient to ensure that the product is characteristic of SEQ ID Nos 1-10 or variants as defined above, and so is not present in other sequences, in particular plant sequences. Where more than one sequence is amplified, they may be selected to be of differing sizes, so that they may be easily differentiated during detection, using techniques such as separation on the basis of size, or melting point analysis.

If required, the kit may further comprise one or more additional reagents necessary to carry out a nucleic acid amplification reaction. Thus it may include enzymes such as polymerases, salts such as magnesium or manganese salts, buffers and nucleotides as would be understood in the art.

The kits may, if required, include means for detecting the products of the amplification. Such means may include dyes or probes, in particular labelled probes that bind the target sequence intermediate the primers. Alternatively, the primers themselves may be labelled to facilitate detection.

Suitable nucleic amplification reactions include reactions that utilise thermal cycling such as the polymerase chain reaction (PCR) and ligase chain reaction (LCR) as well as isothermal amplification reactions such as nucleic acid sequence based amplification (NASBA), strand displacement amplification (SDA), transcription mediated amplification (TMA), loop-mediated isothermal amplification (LAMP) and rolling circle amplification, 3SR, ramification amplification (as described by Zhang et al., Molecular Diagnosis (2001) 6 No 2, p 141-150), recombinase polymerase amplification (available from TwistDx) and others. In a particular embodiment, the nucleic acid amplification is a PCR, and may be a quantitative PCR (QPCR) to provide information regarding the extent of colonisation.

In an alternative embodiment, the amplification is LAMP reaction. LAMP assays utilise at least four and suitably six primers which are designed to target six different regions of the target sequence. There will always be two outer primers (F3 and B3) and two inner primers (FIP and BIP). Optionally, in addition there are two loop primers (FLoop and BLoop). The use of the Loop primers usually reduces the amplification time and increases the specificity of the assay. FIP and BIP primers consist of F2, complementary to the F2c region of the template sequence, and F1c, identical to the F1 region of the template. Four main features need to be considered in order to guarantee a successful LAMP primer design: the melting temperature of the primers (Tm), given 55-65° C. for F3, FIP, BIP and B3 primers and ≥65° C. for FLoop and BLoop; a GC content of 50-60% in the primer sequences; the absence of secondary structures formation and stability at the ends of each primers; and finally the distance between primer regions. Examples of suitable LAMP primer sets are disclosed hereinafter.

The presence of the products of amplification reactions may be determined using any available technology. Thus they may include techniques where products are separated on a gel on the basis of size and/or charge and detected such as agarose gel electrophoresis. Alternatively, they may be detected in situ, using for example using intercalating dyes or labelled probes or primers. The detection of amplification products using a wide variety of signalling and detection systems is known. Many of these systems can be operated in 'real-time', allowing the progress of amplification to be monitored as it progresses, allowing for quantification of the product. Many such systems utilise labels and in particular fluorescent labels that are associated with elements such as primers and probes used in the amplification system and which rely on fluorescent energy transfer (FET) as a basis for signalling. A particular form of such fluorescent energy transfer is fluorescent resonance energy transfer or Forster resonance energy transfer (FRET) for signal generation.

A major example of such a process used commercially is the TaqMan® process, in which a dual-labelled probe, carrying both a first label comprising a fluorescent energy donor molecule or reporter and a second label comprising a fluorescent energy acceptor molecule or quencher, is included in a PCR system. When bound to the probe, these molecules interact so that the fluorescent signal from the donor molecule is quenched by the acceptor. During an amplification reaction however, the probe binds to the target sequence and is digested as the polymerase extends primers used in the PCR. Digestion of the probe leads to separation of the donor and acceptor molecules, so that they no longer interact. In this way, the quenching effect of the acceptor is eliminated, thus modifying emissions from the molecule. This change in emission can be monitored and related to the progress of the amplification reaction.

Where more than one nucleic acid sequence is detected, the kit may comprise components sufficient to carry out multiple separate amplification reactions, such as individual sets of primers. Preferably however the kit is set up to carry out a multiplex reaction, where multiple targets may be detected in a single reaction. In this case, where the detection is done using gel electrophoresis, the primers are suitably selected so that each amplified product has a significantly different size or charge so that they may be readily separated and identified on an agarose gel, or by melting point analysis using a signalling reagent such as a DNA intercalating dye.

Alternatively, where the detection system includes labels, any labels provided for example on primers or probes, will provide a different and distinguishable signal from other primer sets, for example on the basis of the wavelength of the emitted signal and/or the fact that the product has a different melting point or annealing temperature, which may be distinguished by carrying out a melting point analysis of products.

Suitable amplification primers, in particular for PCR amplification, together with the approximate size of the products they generate are selected from those set out in Table 3 below:

TABLE 3

| | SEQ ID | Forward | SEQ ID | Reverse | Product size |
|---|---|---|---|---|---|
| A | 14 | TGAAATTGACGCCCGTTGGA | 15 | CACGCCGGGAAAGAGGATTC | 472 bp |
| B | 16 | GGCAACGCGGTTTCTACGAA | 17 | CGTTAGCCGGGGTTGTCAGA | 489 bp |
| C | 18 | TCGTTGCCACTTTCCGAGGG | 19 | GTCGATTGTGTGCAGCGTCAA | 268 bp |
| D | 20 | CACCGATCTTGTGCGTTTCG | 21 | CGGCAATGCTCCATACCCAC | 522 bp |
| E | 22 | CACCGGAAAGAGTGGCAGGA | 23 | AACCGGGTCACTTGCGTCAT | 783 bp |
| F | 24 | AGCCATCGGAGTCACATCGG | 25 | GGAAACCTCGAAACCCTGCG | 1129 bp |
| G | 26 | TCAGGGCAATCACTAGCCGG | 27 | TCGAGCAGCCGTTTCATCCA | 1118 bp |
| H | 28 | TGATGCGCTTGTTCGTGACG | 29 | CGTTCGCCCTTGTCGTCATG | 478 bp |
| I | 30 | GGGCCATCCGTTACCTGCTT | 31 | TGACACACCCGCTCCGAAAT | 1102 bp |
| J | 32 | GCATTTGCGGTAAGTCATCCCA | 33 | GGATCCCGATTTGCAAGCCA | 814 bp |
| K | 34 | TGTCGGGTCGGGAACTCAAG | 35 | CGGGTTCTCGCTGATGACCT | 464 bp |
| L | 36 | TCCCGCCTGCATCTGAAGAC | 37 | CAGCGATGCCAGCCAATACC | 1098 bp |
| M | 38 | GTTCGTCGCGTCTGATGCAG | 39 | ACCTGGGCATTGTTGGTGGA | 1045 bp |

Primer sets represented by SEQ ID NOS 14-33 have been found to act as useful strain-specific primers for beneficial strains of Gd, while primer sets represented by SEQ ID NOS 34-39 act as useful Gd species-specific primers.

The kits may be used in methods for determining the presence in a sample of a strain of *Gluconacetobacter diazotrophicus* (Gd) able to intracellularly colonise plant cells, said method comprising detecting in said sample at least one nucleic acid sequence selected from SEQ ID NOS 1-10.

Suitably up to 10, for example up to 5 such as about 3 of said nucleic acid sequences of SEQ ID NOs 1-10 are detected.

The method may further comprise detecting at least one nucleic acid which is characteristic of Gd species, as described above, such as a nucleic acid sequence of SEQ ID NOS 11-13. Again, more than one such species specific nucleic acid sequence may be detected if required.

In addition, the method may further comprise detecting a plant specific nucleic acid sequence, which may be characteristic of the particular Gd colonised plant being examined or may be universally present in plants, such as a chloroplast specific nucleic acid sequence, as a control for the reaction.

Various methods of detection may be used in the method, as described above, but in particular, the method comprises a nucleic acid amplification reaction, such as the polymerase chain reaction (PCR).

Suitable primers are as described above.

The sample which may be used in the method of the invention may be any sample that contains or is suspected of containing a strain of Gd. This may include cultures or laboratory samples, which may contain the desired strain of Gd. Alternatively, they may comprise plant samples, including leaf, stem, or root samples, from which nucleic acid has been released, for example by causing cell lysis, for example using mechanical, chemical or sonic means. In particular, the sample is from a plant to which a strain of *Gluconacetobacter diazotrophicus* (Gd) has previously been applied. In this way, the successful colonisation of the plant by Gd can be confirmed.

Typically, such tests will be carried out in a laboratory, although mobile testing, for example, in field conditions, may be carried out if suitable equipment, such as mobile PCR machines, are available, or if detection of targets in particular protein targets, using techniques such as ELISAs, which may be carried out on lateral flow devices are employed.

DETAILED DESCRIPTION OF THE INVENTION

The invention will now be particularly described by way of example with reference to the accompanying figures which are described as follows:

FIG. 1A: is a gel showing PCR products from a range of designed to be strain or species specific, including primer sets A-H in Table 3 (shown in lanes 4, 5, 6, 7, 8, 9, 12 and 13 respectively).

FIG. 1B is a gel showing PCR products from a range of designed to be strain or species specific, including primer sets I-M in Table 3 (shown in lanes 4, 5, 9, 12 and 13 respectively).

FIG. 2: is a gel illustrating PCR products using Primer set E following inoculation of reactions with 100 ng of (1) OSR var. Ability, (2) OSR var. Extrovert, (3) rice var. Valencia, (4) wheat var. Willow, (5) grass var. Aberglyn, (6) grass var. Dickens, (7) maize, (8) quinoa, (9) *Arabidopsis* var. Columbia, (10) barley var. Chapeaux, (11) grass var. Twystar, (12) grass var. J Premier Wicket, (13) potato, and (14) tomato. Lane (15) contains amplicon produced from 10 ng genomic DNA from Gd, (16) contains the no template PCR control, and the molecular weight marker at each end of the gel is Hyperladder 1 kb plus (Bioline).

FIG. 3: is a gel illustrating the sensitivity PCR using Primer set B in reactions containing 100 ng DNA from OSR var. Ability, co-inoculated with (1) 1 ng, (2) 100 picogram, (3) 10 picogram, (4) 1 picogram, (5) 100 femtogram, (6) 10 femtogram, and (7) no added genomic DNA from Gd. Lane (8) is the no template control sample and molecular weight marker at each end of the gel is Hyperladder 1 kb plus (Bioline).

FIG. 4A is a graph showing positive amplification of *Gluconacetobacter diazotrophicus* by fluorescent LAMP using the Genie II real-time machine and a primer set embodying the invention. Positive DNA amplification is detected by a fluorescence signal. FIG. 4B is an anneal curve for the *Gluconacetobacter diazotrophicus* samples, following amplification by LAMP; the reaction was put through an anneal analysis and the temperature at which the dsDNA reanneals is detected as a burst of fluorescence.

FIGS. 5A-C are graphs showing representative results of QPCR experiments carried out using primers designed to amplify sequences according to the method of the invention, when carried out using serial dilutions of samples containing GD DNA. FIG. 5A shows the results for primer set designated P5 for SEQ ID NOs 58 and 59. FIG. 5B shows results for a primer set designated P8 for SEQ ID NOs 60 and 61. FIG. 5C shows results for a primer set designated P17 for SEQ ID NO 62 and 63 as defined hereinafter.

FIGS. 6A-F are graphs showing representative results of QPCR experiments carried out using primers designed to amplify sequences that may be detected using a kit of the invention, when carried out using serial dilutions of samples containing GD DNA and plant genomic DNA. FIG. 6A shows the results for primer set designated P5 in the presence of wheat DNA. FIG. 6B shows melt peak graphs of the products of FIG. 6A for all the samples (i.e. dilutions of Gd in presence of wheat genome and relevant controls). FIG. 6C shows melt peak graph of the controls from FIG. 6A where a positive control comprising Gd DNA only resulted in giving signal, and negative controls comprising plant DNA only and QPCR negative samples only (NTC—no transcript control), both did not resulted in giving signal. FIG. 6D shows results for a primer set designated P17 as defined hereinafter in the presence of maize DNA. FIG. 6E shows the melt peak graph of the products of FIG. 6D for all the samples tested (i.e. dilutions of Gd in presence of Maize genome and relevant controls). FIG. 6F shows the melt peak graphs of the controls from FIG. 6D where a positive control comprising Gd DNA only resulted in giving signal, and negative controls comprising plant DNA only and QPCR negative samples only (NTC—no transcript control), both did not resulted in giving signal.

FIG. 7 shows a resolved 1% agarose gel showing plasmid DNA extracted from a particular strain of GD (IMI504853).

FIG. 8 shows resolved 1% agarose gel restriction digestion product of plasmid DNA with EcoRI from strain of Gd (IMI504853). The restricted fragments are mentioned as 1) ~12 Kb and 2) ~5.6 Kb when run alongside 1 kb ladder where the nearest fragment from the ladder is highlighted for the size comparison.

However, it will be apparent to one skilled in the art that the specific details are not required in order to practice the invention. The following descriptions of specific embodiments of the present invention are presented for purposes of illustration and description. They are not intended to be exhaustive of or to limit the invention to the precise forms disclosed. Many modifications and variations are possible in view of the above teachings. The embodiments are shown and described in order to best explain the principles of the invention and its practical applications, to thereby enable others skilled in the art to best utilize the invention and various embodiments with various modifications as are suited to the particular use contemplated.

EXAMPLE 1

Identification of Unique Sequences

IMI504853, a Gd strain derived from passaging UAP5541, which was found to have particularly beneficial plant colonisation properties was isolated and the full genome sequenced. A comparison was made against the publically available genome of the type strain (PAL5; sequenced by JGI, USA [Genbank sequence accession CP001189]) using standard methods.

Surprisingly, a large number of differences were noted in the genome, and in particular, a number of genes were identified which are present in the genome of IMI504853 but not PAL5.

Many of these genes were annotated with an associated function. The unique genes with annotations were further checked for uniqueness across all the genomes sequenced to date using the NCBI's web-based BLAST tool.

Analysis of the BLAST result narrowed the list to 20 unique genes not present in any genome. These unique genes appeared to be "strain-specific" for IMI504853.

Also, five sets were found to be unique to the Gd species and will hereafter be referred to as "species-specific" (i.e. present in IMI 504853, Pa15 and other Gd strains but in no other species).

Thus these sequence differences appear to characterise the strain and can be used to design a diagnostic kit for IMI504853 and similar strains.

EXAMPLE 2

PCR Validation

Figure 1A:
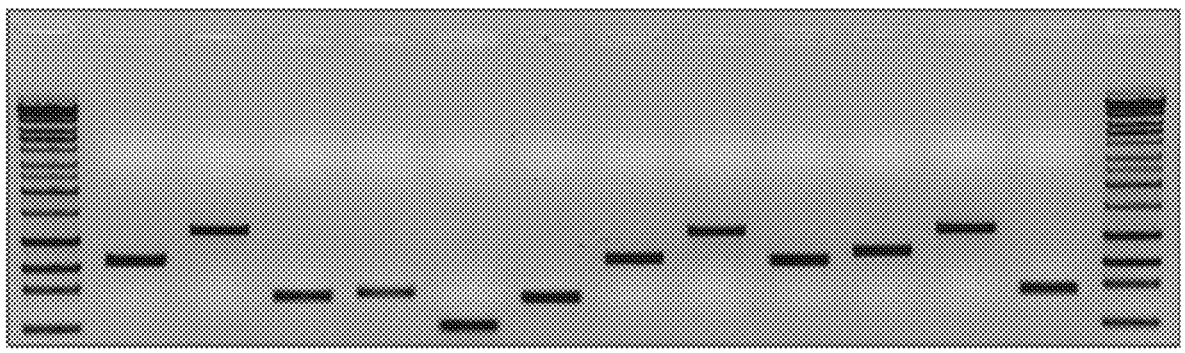
Figure 1B:
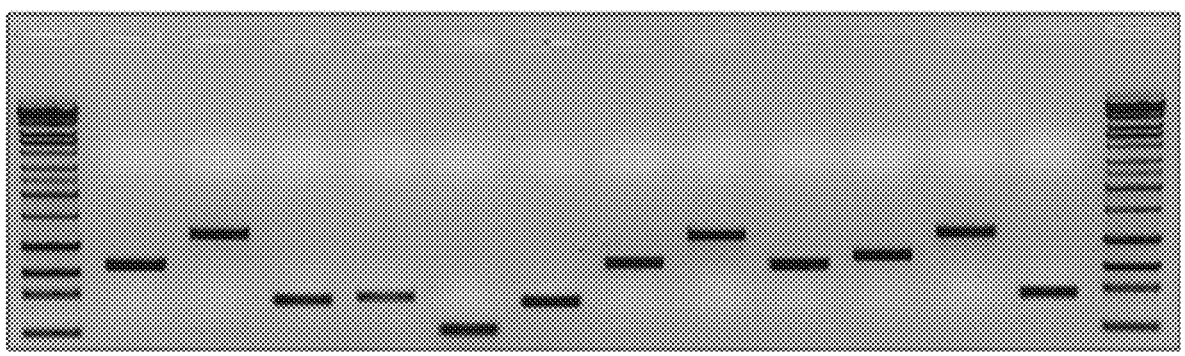

A set of 25 primer sets were designed based upon the sequences identified in the analysis of the genome. The specificity of these 25 primer sets (20 designed to be strain-specific and 5 designed to be species-specific) were first tested by carrying out a conventional PCR reaction using genomic DNA of IMI504853 and PAL5. The results with IMI504853 are illustrated in FIGS. 1A-B. Results showed that 16 strain-specific primer sets delineated IMI504853 from PAL5 as obtained from three different collections (ATCC49037, DSM5601 and LMG7603). However, 4 putative strain-specific primer sets cross-reacted with at least one PAL5 and hence were removed from strain-specific study.

All 5 species-specific primers reacted as expected.

Further, testing of strain- and species-specific primers was done against two other strains of Gd, one originally isolated in India (IMI 502398) and the other from Mauritius (IMI 502399), as well as a revived 2001 culture of UAP5541 strain (stored in glycerol at −80° C.), using the method described above. The data was in agreement with the 16 strain specific primers and 4 species specific primer sets as one of the species-specific primer sets produced a higher molecular weight band. This was a surprise result.

The sensitivity of detection of all 25 primer sets (20 strain-specific and 5 species-specific) was checked using serial dilutions of bacterial broth cultures. It was found that 24 of these sets produced very high levels of detection (requiring 1-10 bacterial cells).

Further, these 25 primers were then checked for cross-reactivity with several target plant species and varieties using DNA extracted in-house. The primers were tested in a PCR reaction using DNA extracted from plants of the following species: maize, wheat (var. Willow), quinoa, rice (var. Valencia), barley (var. Chapeaux), potato, *Arabidopsis* (var. Columbia), oilseed rape (vars. Ability and Extrovert) and a range of grasses (vars. Aberglyn, Dickens, J Premier Wicket, and Twystar). The method for isolating nucleic acids from plant tissues involved the mechanical maceration of leaf material followed by a modified CTAB extraction (Doyle and Doyle, 1987 Phytochem. Bull., 19: 11-15). Briefly, cellular membranes were disrupted using SDS and CTAB to release their contents, and cellular proteins were degraded or denatured using proteinase K and β-mercaptoethanol. The extraction buffer also contained PVPP to remove plant polyphenols, EDTA to chelate metal ions, sodium chloride to solubilise nucleic acid structures, as well as TRIS HCl to stabilise the buffer pH. RNA molecules were degraded using RNase A treatment. Following the removal of insoluble cellular debris using chloroform:isoamyl mix (24:1), deoxynucleic acids were precipitated in ethanol using sodium acetate, washed using diluted ethanol, and resuspended in molecular grade water.

Figure 2:
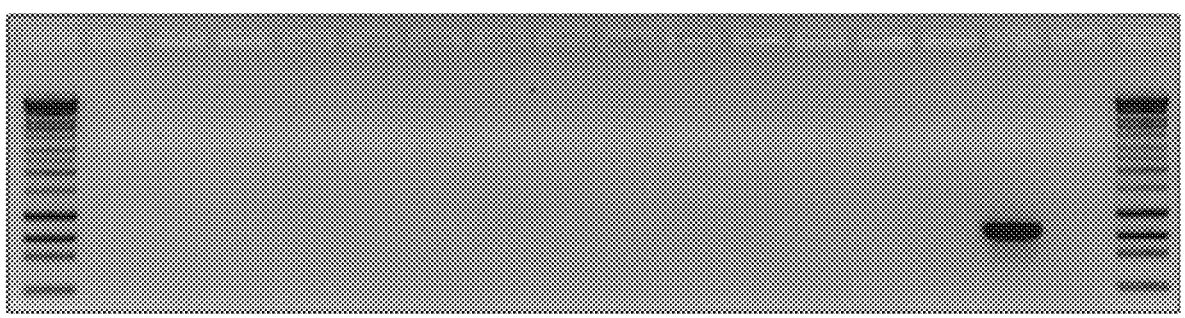

Illustrative results are shown in FIG. 2.

At the same time, the sensitivity of primers were tested by co-inoculating PCR reactions containing 100 ng of the above mentioned plant genomes with six-fold serially diluted genomic DNA from Gd, starting from 1 ng. It was found that the sensitivity of the PCR system was generally unaffected by the presence of plant genome and routine detection was established from a minimum of 1 picogram of Gd DNA.

Figure 3:
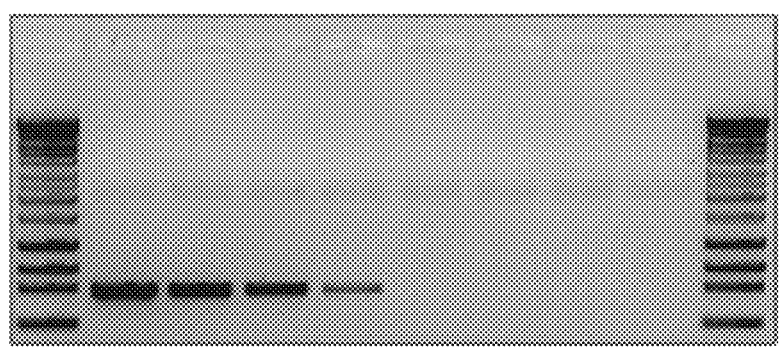

Illustrative results are shown in FIG. 3. Results suggested that 17 of the 20 strain-specific primer sets and three of the five species-specific sets either do not cross react with any plant genomes tested, or cross-react with a small number but produce a DNA product of a different size and distinguishable size.

Of the strain-specific primer sets, only 10 produced results which were of (1) high specificity, (2) high sensitivity, and (3) produced no cross-reactions with plant DNA and these are represented in Table 3 above as primer sets A-J. Similarly only three of the selected species-specific primer sets were found to be specific and sensitive enough for use and these are shown as primer sets K-M in Table 3 respectively. In addition, the size of the products obtained using these primers is shown in Table 3 and illustrated in FIGS. 1A and 1B. Thus, methods and kits based upon these primers are particularly useful in identifying beneficial Gd in field situations.

EXAMPLE 3

LAMP Assay

A series of LAMP primers were designed to amplify regions of SEQ ID NOS 6, 7 and 9 and are shown in Table 4 below as follows:

TABLE 4

| SEQ ID NO | Sequence | Type |
|---|---|---|
| 40 | CTCAGGAAGACCGAATTGATTA | F3 |
| 41 | GCGAAACGTCTGATTGAAC | B3 |
| 42 | CGGATAACCACTGGTGCTCCGACTCGCCTCACTCTACT | FIP |
| 43 | TCCACGAATCTCACGAAGCACCCCGACCTTATCTCCCAT | BIP |
| 44 | GCCAGGCGTGTACATATAACTA | FL |
| 45 | CGGAATACCTAGTTGGAACACT | BL |
| 46 | TCAAGATCGATGCACCTATTC | F3 |
| 47 | AACAGACAGTTCTGGTAGGA | B3 |
| 48 | CGCATCTCCAGATCGGCAGGTCGTCCAGTCGATCATG | FIP |
| 49 | ACATCTGTCCACGGCATTGGTGGCTGGCTTATGAGTCT | BIP |
| 50 | GAGAAGTCCTCTGCTTCGG | FL |
| 51 | CGGCGGTTGAGAAGATGT | BL |
| 52 | GGAAGACATCAACGAAGCA | F3 |
| 53 | TTGACAGTTGCATAGTCCG | B3 |
| 54 | ATACGGCTCGTCATGTCGCGGTGATGGATAATCTCAGCC | FIP |
| 55 | CAGTGGCCGAACCTGGAAGCGCTGATATAAGCCTGAAGAT | BIP |
| 56 | ATTGCACCGCGTTGATG | FL |
| 57 | GCGTAACGGTCACAAGGA | BL |

SEQ ID NOS 40-45 were designed to amplify SEQ ID NO 6 above, SEQ ID NOS 46-51 were designed to amplify SEQ ID NO 7 above, and SEQ ID NOS 52-57 were designed to amplify SEQ ID NO 9 above.

These primers were obtained and tested in a LAMP assay on samples comprising pure Gd DNA that had been isolated using a modified CTAB methodology from bacteria grown in liquid culture.

In addition, DNAs from a range of plant pathogenic bacteria and fungi was tested for amplification in LAMP by the primer sets. These included *Bacillus subtilis, Lactobacillus, Fructobacillus, Pseudomonas* spp., *Agrobacterium* spp., a range of phytoplasmas and various fungi including species from the *Fusarium, Penicillium* and *Aspergillus* genera.

Real-time LAMP was carried out on a Genie II instrument (OptiGene), and 1 µl of sample was added to a 24 µl reaction mix containing 15 µl Isothermal Master Mix ISO-001 (OptiGene), 200 nM of each external primer (F3 and B3), 2 µM of each internal primer (FIP and BIP) and 1 µM of loops primer (FLoop and BLoop). RT-LAMP reaction consisted of 30 minutes of isothermal amplification at 63° C. To evaluate the annealing temperature of the products, reactions were then subjected to a slow annealing step from 95 to 68° C. (0.05° C./s) with fluorescence monitoring.

Negative reaction controls, consisting of water, were also used.

Figure 4A:
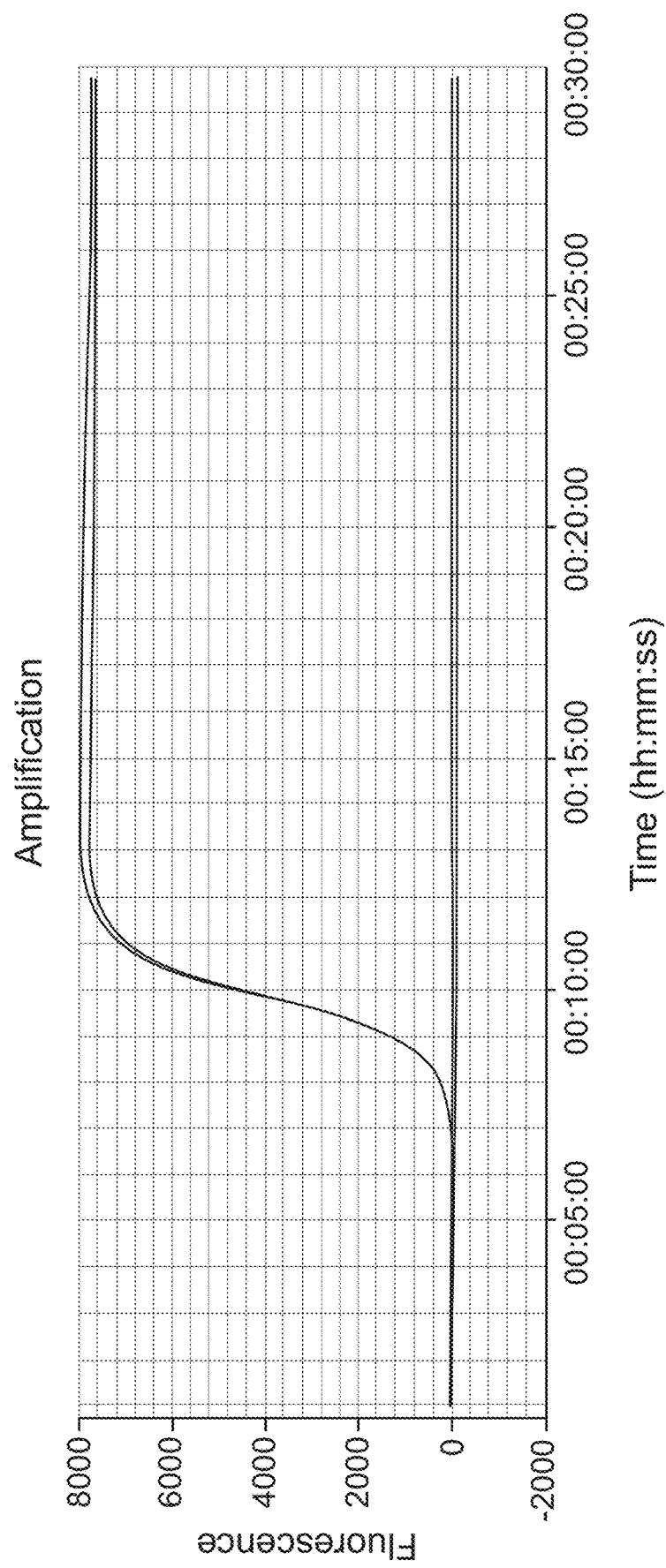
Figure 4B:
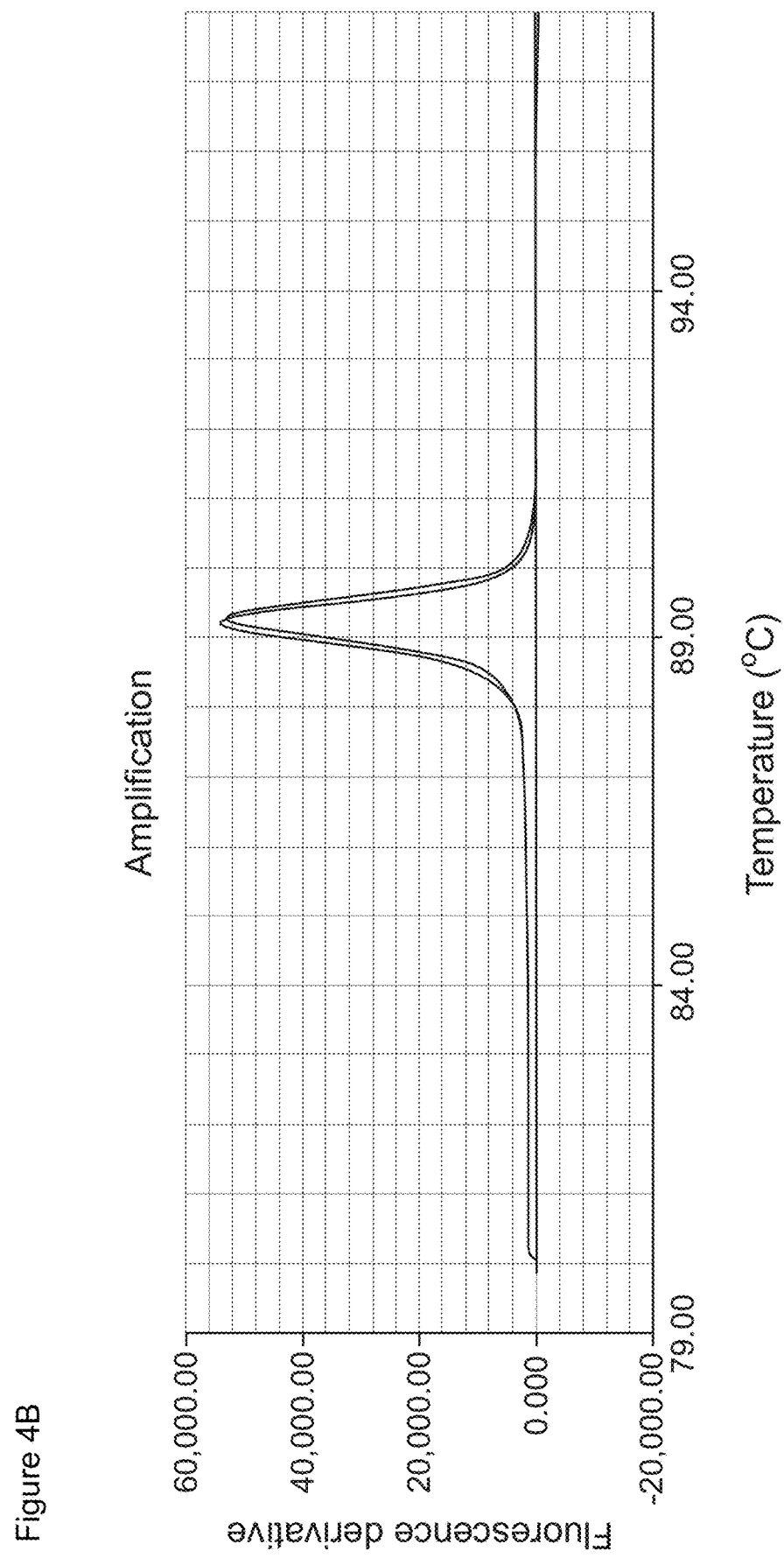

Of the three sets of primers tested in LAMP, the third primer set specific for SEQ ID NO 9 gave amplification in nine and a half minutes with an anneal at 89.2° C. (see FIG. 4A). The primer set specific for SEQ ID NO 6 amplified the positive control at around 11 minutes with an anneal of approximately 88° C., and the primer set specific for SEQ ID NO 7 was the slowest, amplifying the positive control at around 23 minutes with an annealing temperature around 90° C.

All sets of primers that gave the positive Gd amplification were specific for the bacterium and did not amplify from DNA of any of the other bacterial and fungal DNAs they were tested on. They are therefore all suitable as primer sets to be used for detection of the Gd bacterium.

EXAMPLE 4

Detecting Gd on Plant Samples Using LAMP

To validate the primers on rapidly extracted DNA from contaminated seed, a series of experiments were set up in which seed of two plant species, tomato and wheat, were spiked on the surface with Gd DNA. The samples were then put through the 2-minute DNA extraction technique in which the samples are placed in plastic tubes containing steel beads and TE buffer and shaken vigorously for 2 minutes. Two microliters of the solution was then placed in the LAMP reaction as described in Example 4 using the primer set comprising SEQ ID NOs 52 to 57 to test for amplification of the Gd DNA from these samples.

The results showed that the Gd DNA is detectable when put through these assays, against a background of plant DNA.

In order confirm that any samples that tested negative for Gd supported LAMP amplification (i.e. they do not contain inhibitors of LAMP reactions), the cytochrome-oxidase gene (COX) primers (Tomlinson et al., 2012 *Journal of Virological Methods,* 191: 148-154.), which amplify DNA from the host plant, were used as controls for false negatives on all samples.

EXAMPLE 5

QPCR Determination

A range of QPCR reactions were carried out on samples comprising known quantities of DNA from Gd (IMI504853) and also from a range of crop species including maize, barley and wheat genomic DNA.

QPCR reaction mixtures were prepared to a volume of 20 µL volume per reaction. In the case of Gd DNA alone, these consisted of 10 µL iTaq™ Universal SYBR Green® Supermix (2×) (Bio-Rad), 1 µL each of forward and reverse primers (final concentration of 10 µmol), 7 µL SDW (sterile distilled water) and 1 µL DNA template at the required concentration.

Primers used in this case were as set out in Table 5.

TABLE 5

| SEQ ID NO | Sequence | Type |
|---|---|---|
| 58 | AGGAGGCTCTTTCTTTGGAAGC | Forward |
| 59 | AAGTGCCCCTGTTATCGTACAC | Reverse |

TABLE 5-continued

| SEQ ID NO | Sequence | Type |
|---|---|---|
| 60 | TGGGTCATCGGTTCTGATTTCC | Forward |
| 61 | TAGTTTGATGTCGGGTGCTGAG | Reverse |
| 62 | GCGAATACCGGTCTTTTTACGC | Forward |
| 63 | ATGCAAGCTCCGGATTGAGAG | Reverse |

The primer set represented by SEQ ID NOs 58 and 59 (designated P5) was aimed at amplifying a 149 base pair region of SEQ ID NO 3, the primer set represented by SEQ ID NOS 60 and 61 (designated P8) was designed to amplify a 104 base pair region of SEQ ID NO 6 above, and the primer pair represented by SEQ ID NO 62 and 63 (designated P17) was designed to amplify a 130 base pair region of SEQ ID NO 10 above.

Thermocycling was carried out using a CFX96 Touch™ Real-Time PCR Detection System from Bio-rad. Initial denaturation was performed at 95° C. for 3 minutes; amplification was performed using 40 cycles of denaturation at 95° C. for 5 seconds followed by 60° C. for 30 seconds (plate read post each amplification).

Figure 5A:
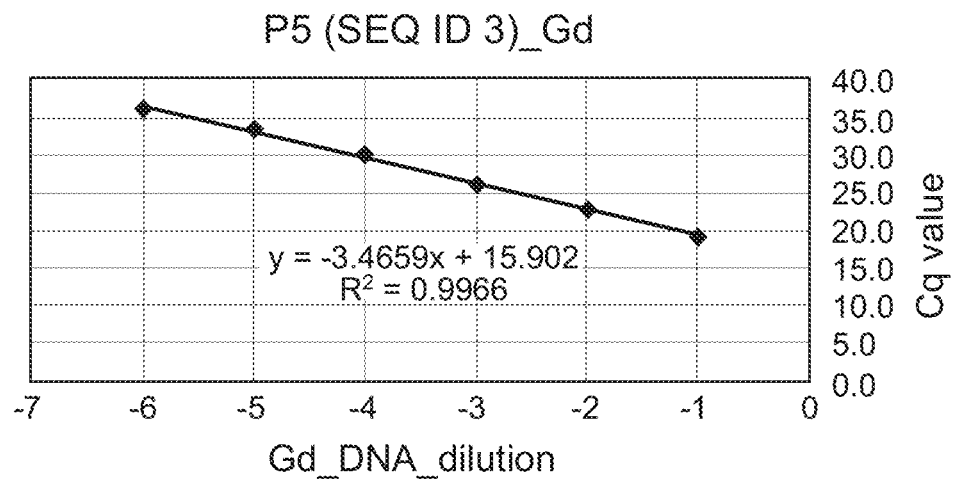
Figure 5B:
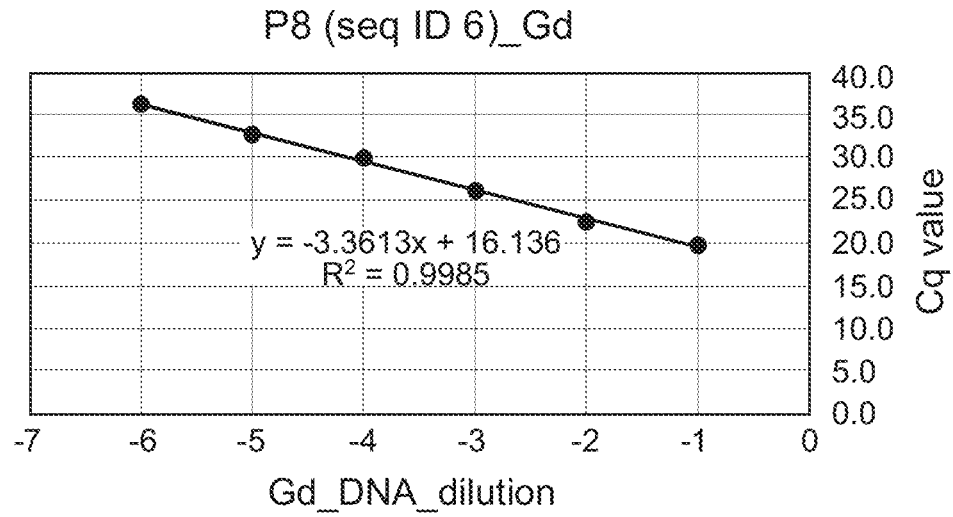
Figure 5C:
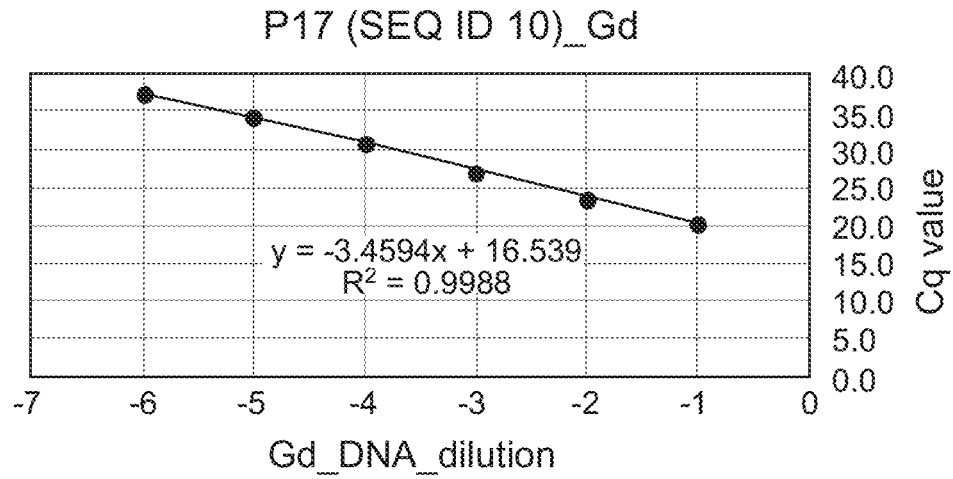

All of the primer sets amplified Gd DNA with good efficiency as set out in Table 6, which shows the average Cq values of three replicates of the amplification, and quantitatively as illustrated by FIGS. 5A-C. The percentage efficiency was calculated using the formula % $E=[10^{-1/slope}]-1\times 100$.

TABLE 6

| Log Dilutions | P5 (SEQ ID NOs 58 + 59) | P8 (SEQ ID Nos 60 + 61) | P17 (SEQ ID NOs 62 + 63) | ng/μl |
|---|---|---|---|---|
| −1 | 19.23 | 19.68 | 19.96 | 12 |
| −2 | 22.75 | 22.55 | 23.39 | 1.2 |
| −3 | 26.19 | 26.10 | 26.78 | 0.12 |
| −4 | 30.23 | 29.97 | 30.75 | 0.012 |
| −5 | 33.64 | 32.85 | 33.96 | 0.0012 |
| −6 | 36.15 | 36.26 | 37.04 | 0.00012 |
| −7 | NA | NA | NA | |
| Slope | −3.4659 | −3.3613 | −3.4594 | |
| % Efficiency | 94.32 | 98.38 | 94.57 | |

The quantitative amplification was carried out in the presence of genomic plant DNA in order to determine whether there was any cross reactivity. It was found that whilst there was cross reactivity with some plants species, the primer pairs P5 showed no cross-reactivity to wheat and barley genomes, P8 showed no cross-reactivity to wheat barley and maize and P17 showed no cross-reactivity to wheat and maize genomes making these potentially suitable primer sets for detecting Gd in crop species.

To ensure that primer efficiency and robustness would be maintained in the presence of plant genomic DNA, the above QPCR examples above were repeated but in this case, the composition was varied in that 6 μL SDW (sterile distilled water) was used together with 1 μL relevant Gd dilution DNA template and 1 μL plant genomic DNA template. For instance, Gd DNA (92 ng/μl) was serially diluted from $10^{-1}$ to $10^{-7}$ with either wheat DNA (70.6 ng/μl) or maize DNA (111 ng/μl) and amplification reactions run as described above.

Figure 6A:
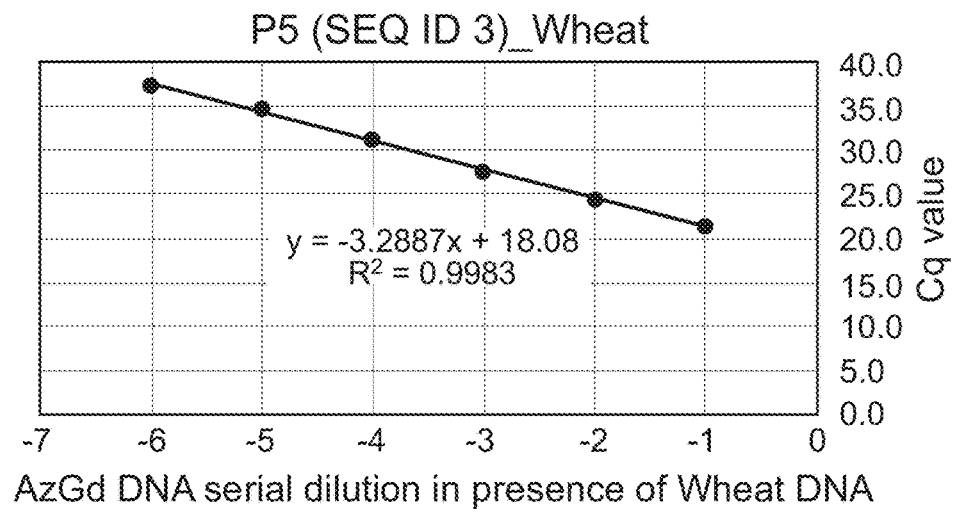
Figure 6B:
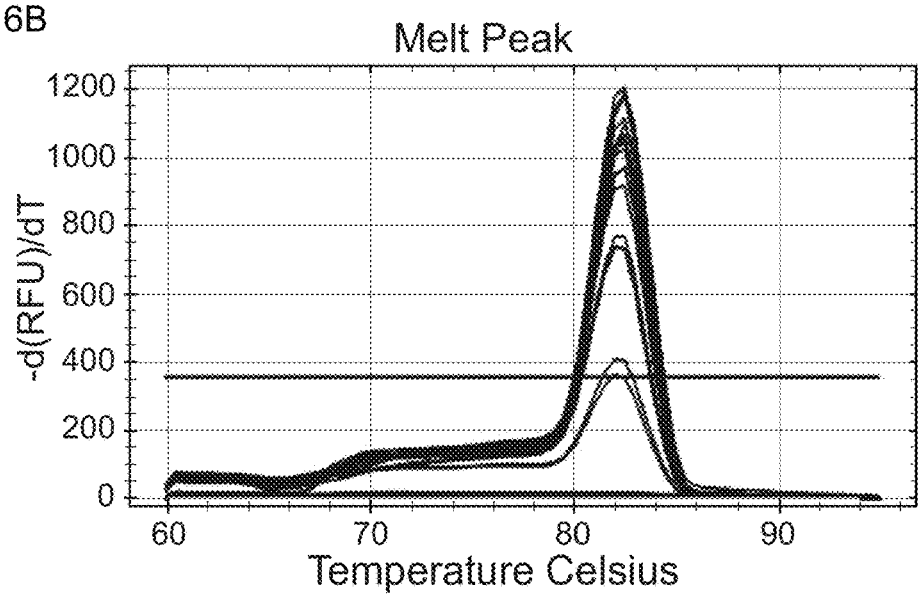
Figure 6C:
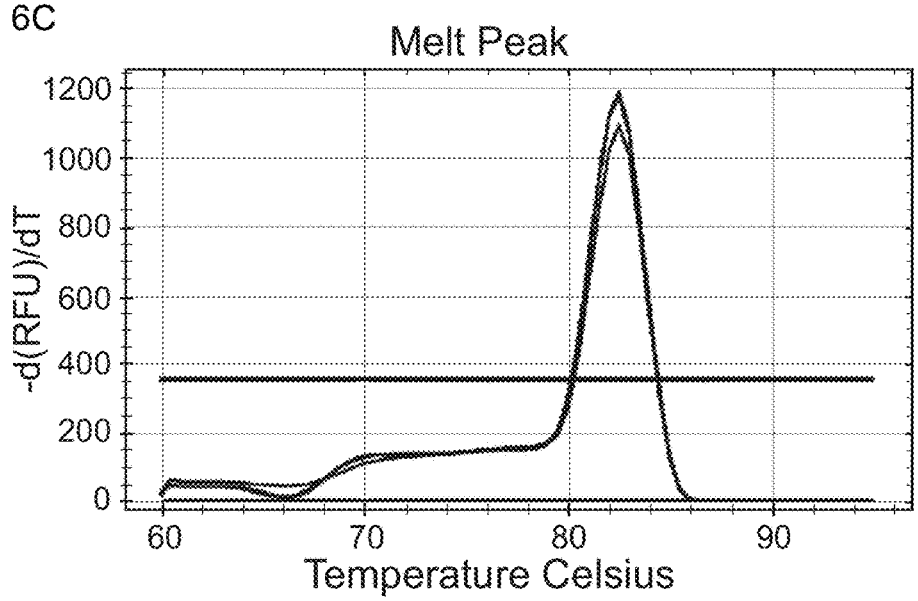
Figure 6D:
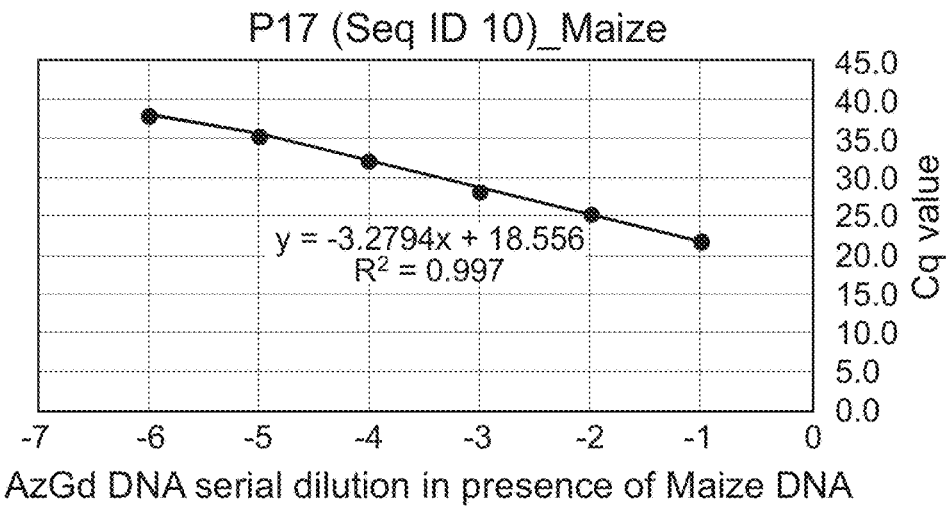

Representative results are shown in FIG. 6A and FIG. 6C and in Table 7.

TABLE 7

Gd + Plant DNA QPCR Std. curve

| | Cq Value from QPCR run | | |
|---|---|---|---|
| Log dilutions | P5 (Seq ID 3)_Wheat | P17 (Seq ID 10)_Maize | ng/μl in reaction |
| −1 | 21.47 | 21.76 | 9.2 |
| −2 | 24.56 | 25.11 | 9.2 |
| −3 | 27.69 | 28.13 | 0.92 |
| −4 | 31.38 | 32.08 | 0.092 |
| −5 | 34.89 | 35.32 | 0.0092 |
| −6 | 37.55 | 37.80 | 0.00092 |
| −7 | N/A | N/A | 0.000092 |
| AzGd DNA (0.01) | 24.20 | 25.00 | |
| Plant DNA | N/A | NA | |
| NTC | NA | NA | |
| Slope | −3.2887 | −3.2794 | |
| % Efficiency | 101.41 | 101.81 | |

It appears that the primers will maintain efficiency in the presence of plant genomes and thus may form the basis of a detection kit.

Results were confirmed by carrying out melt analysis post amplification the denaturation curve (Melt curve) analysis was performed from 60° C. to 95° C. with 0.5° C. increment 5 seconds/step followed by plate read after each increment.

Figure 6E:
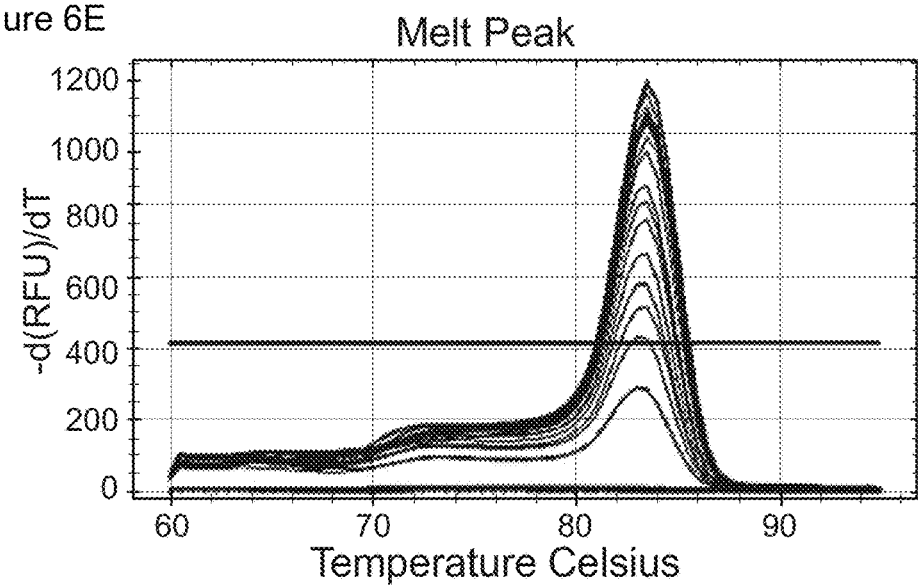
Figure 6F:
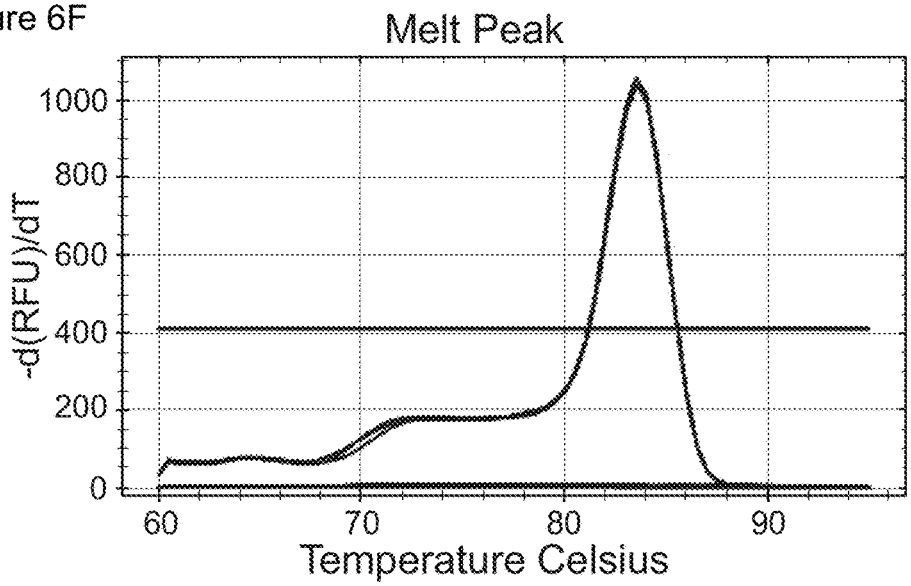

Representative examples of the results are shown in FIGS. 6(B) and 6(E). Clear melt curves are visible for amplified Gd DNA, without plant genomic DNA.

EXAMPLE 6

Plasmid Detection

Figure 7:
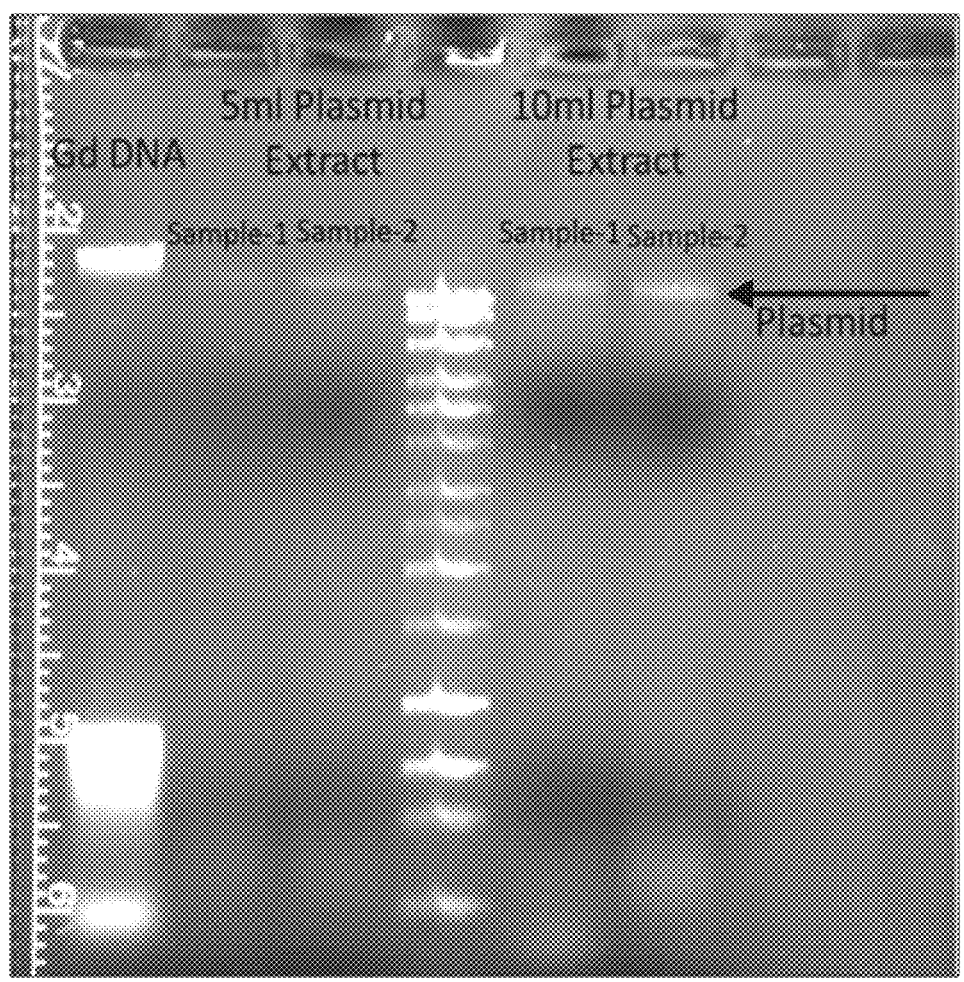

Plasmid DNA extraction from Gd (IMI504853) was performed using Qiagen mini prep kit (Cat. No. 69104). The low copy number plasmid extraction protocol was followed using 5 ml and 10 ml 48 hour bacterial culture. The extracted plasmid was run on 1% agarose gel flanked by a 1 kb ladder (FIG. 7) and imaged.

Alongside the plasmid DNA, genomic DNA of Gd (IMI504853) was also included on lane-1. The results, shown in FIG. 7 indicate the presence of a single plasmid of about 17.5 Kb in size, which is smaller than that reported previously for plasmids found in PAL5.

The plasmid DNA was sequenced and a primer was designed using Primer3 (Untergasser et al. (2012) Primer3—new capabilities and interfaces. Nucleic Acids Research 40(15):e115; Koressaar and Remm (2007) Enhancements and modifications of primer design program Primer3 Bioinformatics 23(10):1289-91) to cover the start and end sites of linear sequence data (P_End_Fw—CCAAATCTCTGGAACGGGTA (SEQ ID NO 64). Sangar sequencing was performed using this primer (SEQ ID NO 64) and the sequenced data was aligned to confirm the plasmid sequence was complete.

Since plasmid DNA in its natural form is circular and can form secondary and tertiary structures, this may impact on the accuracy of size measurements using agarose gels. To confirm the results and also validate the sequencing of the plasmid DNA, a restriction map of plasmid was studied using NEBcutter. The restriction digestion will linearize the plasmid providing only a single conformational structure. Also, the restriction enzyme selection is done after studying the sequence, thus allowing the plasmid sequence to be validated as well. In case of IMI504853 plasmid DNA, the NEB-cutter showed the restriction enzyme EcoRI to digest the plasmid DNA at 3864-9461 bp and 9462-3863 bp producing a DNA fragment of 5598 bp and 11968 bp. Both the size can be studied using a 1 Kb ladder available in the lab, removing the limitation of the reference ladder's maximum size detection as well.

Figure 8:
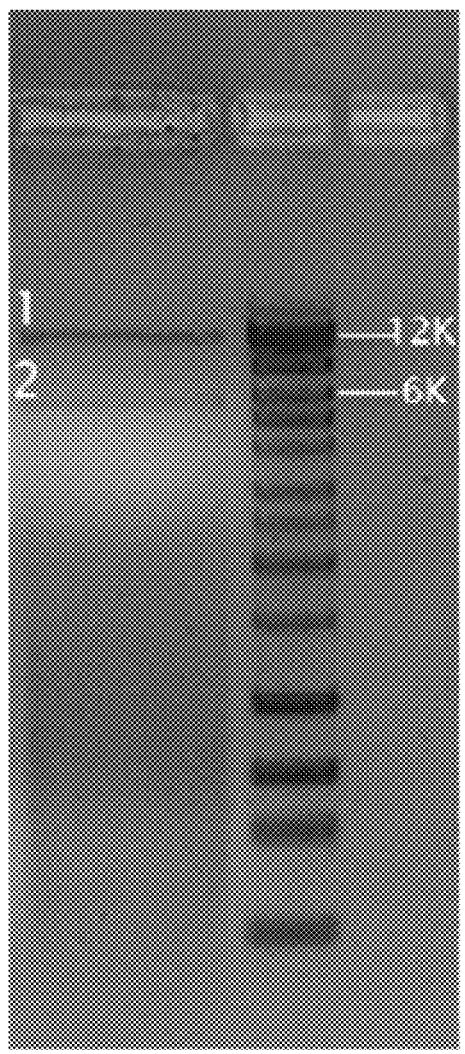

Therefore, restriction digestion was performed on IMI504853 plasmid using double cutter EcoRI (Fisher, cat no—10819360) as per supplier's protocol. Post restriction digestion the products were run on 1% agarose gel until the bands were resolved and imaged. IMI504853 plasmid DNA when restricted with EcoRI produced two fragments (1. ~12 Kb and 2. ~5.6 Kb) of DNA of predicted size (FIG. 8).

This validated the sequencing data in terms of both size and sequence. It may further provide an identification test or a confirmatory test in relation to a kit used in the identification of strains of the invention.

EXAMPLE 7

Illustration of Activity of IMI504853

Figure 9:
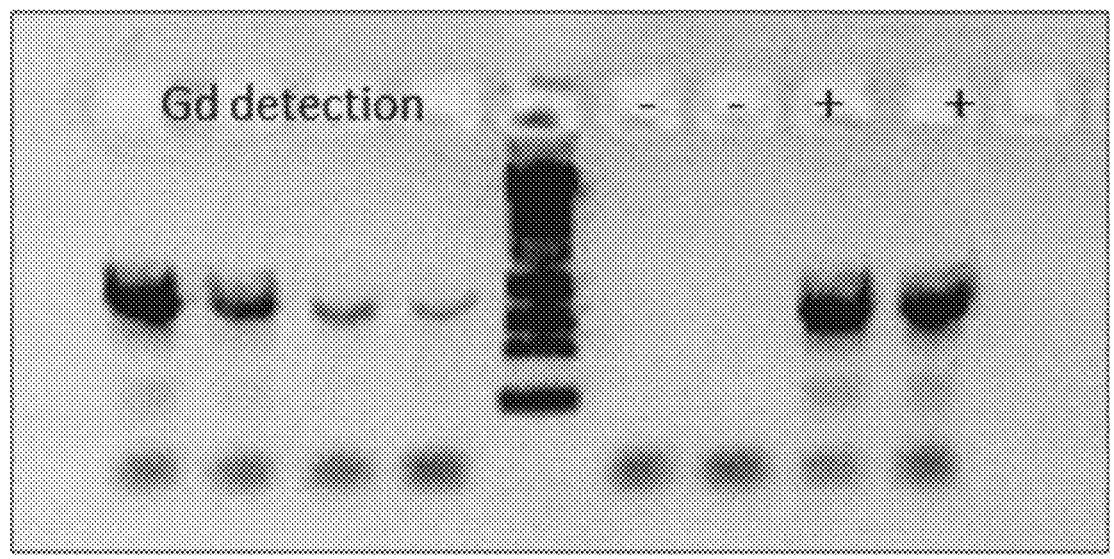
FIG. 9 shows an agarose gel obtained from a PCR amplification to detect Gd from the seedlings of wheat obtained during a field trial.

A field trial was designed to test Gd (IMI504853) as a bio-fertilizer using wheat (cultivar Mulika). Two plots of Gd treated and control (untreated) respectively where planted. Post germination the young wheat seedlings at 10-12 day of growth were sampled and tested for Gd presence using the primer G (seq ID 26 & 27) representing the DNA seq ID 7. The Gd presence was detected when PCR was resolved on a 1% agarose gel with respective negative and positive controls (FIG. 9) confirming that in real world condition the designed kit works well.

Figure 10:
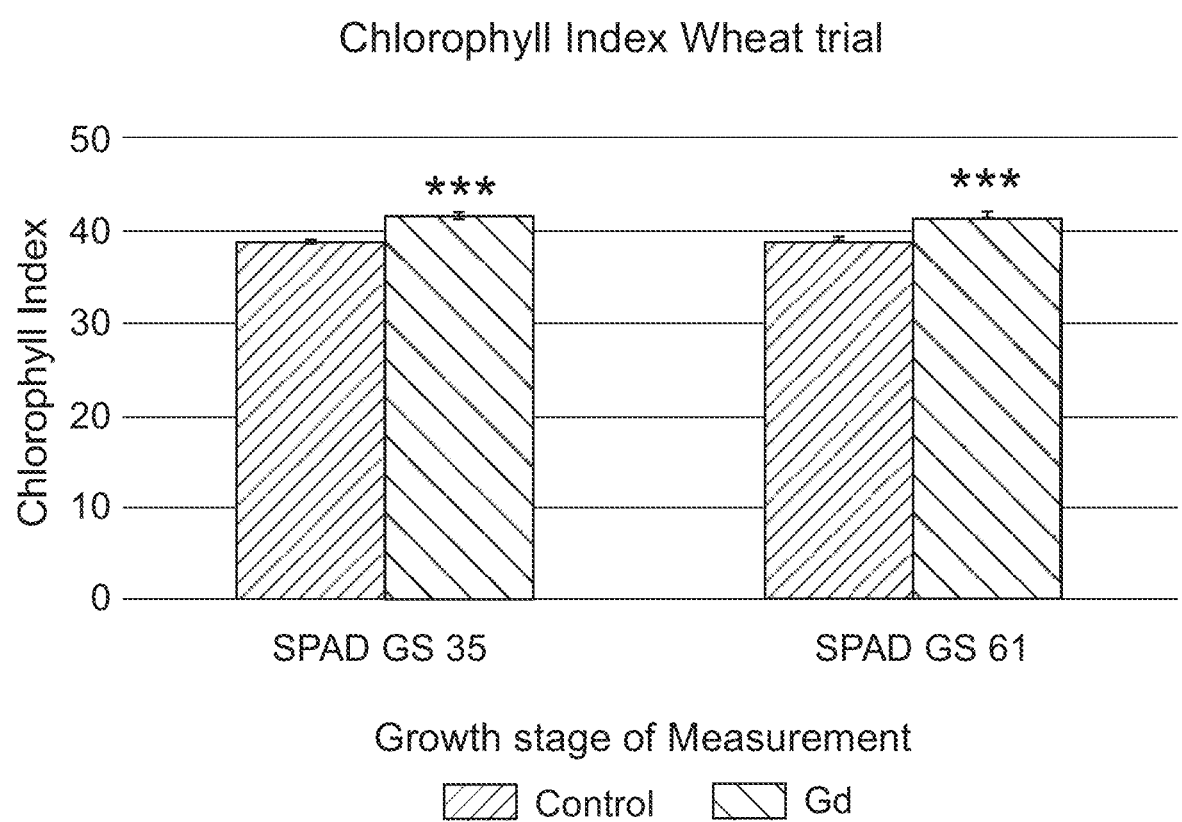
FIG. 10 is a graph showing the chlorophyll index of wheat treated with Gd in accordance with the invention compared to a control.

The measurement of chlorophyll content i.e. "greenness" using a SPAD meter has been shown to correlate with over all plant health and crop yield. The crop at growth stage 35 and 61 were checked for its chlorophyll content using SPAD was found to be statistically significantly (P=0.001) in Gd treated plots when compared to control plots (FIG. 10). Interestingly, the SPAD showed a significant increase in the chlorophyll content from the wheat obtained from plots treated with Gd of the invention compared to untreated controls (FIG. 10). This indicates that Gd treated plots which have been confirmed to have the bacterium present using the diagnostics kit results in much healthier plants and potentially higher yield. The data from wheat field trial indicates the efficacy of Gd as a bio-fertiliser.

EXAMPLE 8

Yield Benefits of use of IMI504853

Forage maize seed untreated and treated with a formulation comprising IMI504853 at a concentration of about $10^5$-$10^7$ cfu/ml was sown at two different locations, and fertilised at different proportions of the recommended rate of nitrogen fertiliser, ranging from 0 to 175 Kg $ha^{-1}$ for each particular variety, region and availability of soil nitrogen. Yield results indicated an overall potential reduction in nitrogen fertiliser of between 40-95% without suffering any yield penalty. Average yield benefits across N levels led to an increase in yield of between 7% and 21%. Thus at full recommended N fertiliser rates IMI504853 treated crops could provide a yield benefit up to 1 t/ha in maize.

In another trial, spring wheat seed, either untreated or treated with a formulation comprising IMI504853 at a concentration of about $10^5$-$10^7$ cfu/ml was sown in Spring. The crop was fertilised at different proportions of the recommended rate of nitrogen fertilizer ranging from 0 to 125 Kg $ha^{-1}$ based on variety, region and availability of soil nitrogen. Across all fertilizer levels, IMI504853 treated crops showed an average yield increase of 15%, but at zero nitrogen fertilizer and full nitrogen fertilizer this increase was 20% and 10% respectively. The results indicate that for the IMI504853 treated crop, it is possible to reduce N fertiliser application by up to 85% and still achieve the same yield as a fully fertilised crop.

TABLE 1

| | | |
|---|---|---|
| SEQ ID 1 | Glutathione S-transferase (EC 2.5.1.18) | ATGACAAAATTATACTATTCTCCCGGCGCTTGCTCTTTGGCAGGGCATATTTTGCTCGAAGAGTTGGGAAGACC<br>ATATGAGTTGAAATTGACGCCCGTTGGAGACGAAGGCACGGGAAGTGAAGAGTTTCTAAAAATAAACCCGCGAG<br>GAAGGGTGCCTGTTTTAATTGATGGTGCGGAAATAATTACCGAAAGCCCCGCAATCTTATTTTATTTATCGAGT<br>TCATTTTCAGACGGAAATTTCTGGCCAAAATCAGTTTTGGAGCAAGCCCGCTGCTGGGAATGGTTTAACTGGTT<br>ATCGAGCAATGTACACTCGGTTGCCTATGGGCAGGTGTGGCGACCAGGACGGTTCATTGATGATGAGCGTCAGT<br>GGAATAATGTTATTTCAAAAGGGAAAAATAACCTTCATGAATTTAGTGATGTAATAGAAAATAATATCTCCGGG<br>AAAACGTGGTGTGTGGGTGAATCGTATTCATGCGTTGATCCGTATTTGTTTGTTTTTTATTCTTGGGGGAAAGC<br>CATCGGATTGGATATGGAATCCTCTTTCCCGGCGTGGTCGCGTCATGCAGCGCGGATGCTGGAGCGGTTGGCCG<br>TTCAAAACGCTTTACGGCAAGAAGGTTTGATCTCGTAA |
| SEQ ID 2 | O-methyltransferase (EC 2.1.1.-) | TTGGATGCCTCTCGTTTTCCTTGCGGAGTCATCATGACCATTCCTCTCTTTCGTCCGCAATTCACACCGCAGAT<br>TCAACGTGCGCTTGATCGCCTTTATTCCGAGACACTCTCGCAAGATCCAGCGATACGCCAATTGGCGCAAGCCA<br>AAGGACTGACACATGACGGGCAACGCGGTTTCTACGAAGCCATGAAAGATGCCAGACTACCCGTTACGCCAGAG<br>TTCGGCGCCCTGCTCTATATTCTGGCACGCAGCACCAGAGCCCAACATATCATCGAATTCGGCACGTCCTTCGG<br>TGTTTCAACATTATTTCTCGCAGCGGCTTTACGCGACAATGGCGGGGGCCGACTGGTGACCTCGGAACTTATCT<br>CAGACAAAGCAGAAAGGGCTTCCGCCAATCTGCGGGAGGCAGGACTGGCAGACCTCGTAGACATTCGCATCGGA<br>GATGCCCGCGCCACGTTATCGCGTGATCTTCCTGAGTCGATCGATCTGATCCTGCTGGATGCGACTAAAGGACT<br>CTACCTCGATCTCTTACTCCTGCTGGAACCTGCATTACGAAAAGGTGGCCTGGTGATCAGCGATCGCGCCGATC<br>TCGATGGTGACGACGGCGGTCGCGCAGCAGCCTACCTTACCTATCTGACAACCCCGGCTAACGGATATCGCATC<br>GCCGGCATCACTACACAGGCGTTGGGACAAACCTTCGCTCACGATGTGGCGGTGCGCACCTGA |
| SEQ ID 3 | Transcriptional regulator, TetR family | GTGGGAATAGCCACGCTCTACCAATACTTTGAGAACAAGGAGAGCGTTGTCGCGGCACTTAGTCGTCGGGTACG<br>GGAAACACTGCTCCATGATGTTGCGTCATTACTCGAAACCGCTTGTTCGTTGCCACTTTCCGAGGGTGTGCGCT<br>GTCTGGTCGTCGCTGCCGTGAAGGCGGACAAGAGCCGTCCATCGCTTACGGTCCGGCTTGATCGGTTGGAGGAG<br>GCTCTTTCTTTGGAAGCGGATCATCTGCTGGTAGCGGCTGAGCTTTGCACGGTTGTTGCGTCGTTCCTCAAGTG<br>CCAGGGAATTATTCAGGAGAACACTGCAAAAATTCTGGCAGATGATCTGTGTACGATAACAGGGGCACTTATTG<br>ACGCTGCACACAATCGACAGATACCTATCGATGACTTGCTAATTGACCGTATTACGCGAAGGCTGGTCGCGATT<br>ATTCAGAGCGCGCTTTAA |
| SEQ ID 4 | RNA polymerase ECF-type sigma factor::RNA | GTGGGACAGCCGGACAAATATTTCGAGCTTTTCGCGATACATCGCACCGATCTTGTGCGTTTCGCCAGAGGTAT<br>CATGAGAGATGATAGTCTGGCGGAAGATGTTGTACAGGATGCTTTTCTGCGGCTGACTACTGTAACAGTGGCAC<br>AGGACCGCGTTCTTTCGGATCCTCTGAATTACGTTTACCGCATTATTCGGAATCTGGCCTTTGACCGTTATCGA |

TABLE 1-continued

| | polymerase ECF-type sigma factor | CGACGGCAATTCGAGGCCGGATTGTTTGACCATGGGGTAGATAGTTCTTCCGAAACAATCGAAGCGGATGCCCC<br>TACACCGGAAGGTGAGGCTTCAGGGAAATCCGACATGCGGGCAATGCGCGCCGCTATGGCGGAACTGCCAGAAC<br>GGACGTGCGTCGCATTGGAAATGCATCTGTTCGACGGACGAAAGCTACGGGAAATAGCGGCTCATTTAGGTGTT<br>TCTATTGGGATGGCCCACTCCCTTGTCGCAGTGGGTATGGAGCATTGCCGCAAACGTCTTTCCACACCTGAAAC<br>CTGA |
| --- | --- | --- |
| SEQ ID 5 | FecR family protein, COG:Fe2+-dicitrate sensor, membrane component; | GTGAGCGAAGACTTCAATCCAACAACGGCGGTTGAGTGGAAAATAGCCCTTTCAGAAGAGCCTGACGATTCTGT<br>GCTCAGAGAACGCTTTGAAGCATGGCTTGCTGCCGCAGAGGATCACCGGAAAGAGTGGCAGGAACTTACGCAGG<br>GACTTGAGAATTTCCGCCAGATTGGCCCGCTTTATCGTGAGAAATGGGTGCCTTCATCAAGTGGGGCACAAAAT<br>ACTGCGTCAAAACAAGGTAGGCTCAAAGGAAGACCTGCTAATTTTGTTAGGTTTTCAGTTGCTGCATTTGCGGC<br>TGCTGCTGCCGTTACATTGGTATGGTCCTCTGACCTTCTGCTTCGATTACAGGCCGATTACGCCACAGGCTCGG<br>CAGAAACGCGAACAGTCAGTCTCCCCGATGGTAGTGAATTGACCCTCGCGCCGCGAAGTGCGGTAAAAATGTCT<br>TACTCTGTAGAGAAACGGGATATTCGTCTTTTAAAGGGAGAGGCGCTCTTCACGGTTCGACATGATATGGCGCG<br>ACCTTTTGAGGTCCACACAGACAAATTCACCGTAACGGACATCGGAACTATTTTTGACGTCAGAATGTCTCAGG<br>GCGAGGAAGAAGTCTCTGTCCGGGAAGGAGAGGTCCGGGTGCAGGATGTTTCCGGTGGATTTCATAATCTCGAT<br>GCCGGAACGTGGGAGCGGATTAGAACTGTAGGCAATGGAGTGAGCGTCACTCATGGGAGCGGCTCTCCGGAAGA<br>TGTGGGCGCATGGTCAGCGGGGCAAATTATTGCCAAGGAAAACAGCGTGTCCAGCGTCGTGGGAAAGGCTTAGGC<br>CCTACTACCGGGGGGTTGTTGTCCTTTATGGTTCTTCCTTTGGGGAGAAGTCACTCACTGGTGTTTATGACGCA<br>AGTGACCCGGTTGGCGCATTTCGGGCGATCGCAGCCGCGCATCATGCTCAGATGCATCAGGTTTCGCCATGGCT<br>GACAATATTGGCCGCACCGTAG |
| SEQ ID 6 | Ferrichrome-iron receptor | ATGAAGGGTGCGGTTGCATTGCATTCGCAATTGTGGCGGCTCATACGAATGGGAACGGATAAGGTGATGACGAT<br>TGATGATAGAATGAAGCGGTGTGGGCGGCAGGTGGCGTGGCTTATCGCGCTGGGTAGTACGACGTTTCTGAATG<br>CCGCTGTGACGAAAAGCTATGGTGCAGAACCTTCCCAAAGTGCTCGGGCCGTCAGATCATTTTCCATTCCGGCC<br>CAATCTCTTGAPGATGGTCTCGCAAGGTTCGGACAGCAAAGTGGGTGGCAGGTTTCTGTTGACGGAAATCTTGC<br>AAAATCTCTGACAACGCACGGTGTTAGCGGTACGATGACATCTGCTCAGGCCCTCAATGCGATCCTGTCCGGGA<br>CTGGCCTGACATACACGATCAGGGGTGGCCGAACCGTCGTGCTGACAAAGCAGTAGCCAACATCACGCTTGGT<br>CCGGTCCGTGTCGGAGGAACCCTCGCGCGTCAGGATCCAACAGGGCCGGGTGTCGGCTACTTCGCCGAAAACAC<br>AATGGTTGGTACAAAGACGGATACGCCCATCACGGAAATACCGAACTCAGTCTACGTCGTGACCAAGCAGTTGA<br>TGACCGATCAGCAGCCGCAGAATATCCTACAGGCTTTGCGTTACACTCCCGGCATCTACTCTGAAGCCGGAGGA<br>ACGACAAATCGCGGATCTGCCCAGAATGACAACATGGGCATTTATCAGCGTGGATTTCTCGAGCCAGTTCGT<br>GGATGGGTTGATGACGAATTCGTATGCCGCCGCCGAGCCAAGCTTTCTGGACCGTATCGAGGCGCTCAACGGTC<br>CAGCATCGGTGATGTATGGCCAGACGACACCCGGAGGAATGGTCGGTATGAGCCTGAAGAAACCCACCGAAACG<br>CCGCTGCATCAGGTTTCGCTAGGCTTCGGAAGCTGGGGACGGTACGAGGCAACGTTCGATGTCAGCGATAAGAT<br>CACGCAGTCCGGTAATCTGCGCTATCGTATTGCAGCCATCGGAGTCACATCGGGCACTCAGGAAGACCGAATTG<br>ATTATCATCGGGTGGGTGTACTTCCTTCAATCACGTGGGATATCGATCCCAAGACTCGCCTCACTCTACTTGGT<br>AGTTATATGTACACGCCTGGCTCAGGGAGCACCAGTGGTTATCCGGTCCTCGGGACTCTTATTCACAATTCGGA<br>AATTCCACGACTCTCACGAAGCACATTTATCGGAATACCTAGTTGGAACACTATGGGAGATAAGGTCGGGATGT<br>TCGAATATCAATTTAGTCATAAATTTAATAAATTTATTGAGTTCAATCAGACGTTTCGCGTAGAGAATTCCAAC<br>GTTCATGAGTCAAATATCACCGATGTAACACCTGTAGATGTTGAAGGAAAATGGACATATTTTTATCCTTGGAA<br>ACAAAATTATGAAAACACAACTGAGGTACTTGATACTCGCTTAGGGGGCGGTTTCTAACTGGTCCTGTACAAC<br>ATACATGGGTCATCGGTTCTGATTTCCGCAATTATGACTATCATTATACTGAGCTCATCGACGACGGTGCGACA<br>ATCGTTGTGCCCACTCAGCACCCGACATCAAACTATTCCCCATGTATAAGTTTAACCTCCGCGAAGTGTGACGC<br>CTTCGCGGGAATAAACCCAGACTATAACTCGTTTCAGGAGGGCGTGTATTTTCAGGACCAGATAAAATGGCAGC<br>GCCTGTCCGTTCTCTTGGGTGGACGCCAAGATTGGGTTAATTCATCTAATAAAAATTACAGTGTAACGAACTTT<br>TATGGAAACGTCAGCACCCGCGTTAATAACACTGCTCCACACCCTCAATCGGCCTTCACCTGGAGAGCTGGTAT<br>AATCTATAATTTTTGACTTTGGGCTTGCCCCGTACTTCAGTTACGCAACATCCTTTGTGCCACAAGGAGGTACGG<br>ATTGGCAGGGTAAGATTTTCGCGCCTTTGAGCGGAAAGCAACTCGAAGCCGGGTTGAAGTATAAAGTTCCAAAC<br>GAAGATATCCTCATAACGGCATCAGCATTCCGAATTGATGAAGACCACTATCTTATCAGTGATCTTGTTCACAC<br>GGGCTTTAGCAGTGACGCGGGAACGGTACGCTCGCAGGGTTTCGAGGTTTCCGCCAGTGCGAACATTACCAAAA<br>ACCTCAAACTTGTCGCCTCTTACACATATGAGGATGTGCGGTTCAGAAAGAACAATTTGGCCGTAAATTCGGTC<br>GATCCCGTCACGCTAACATATGGAGCAAAGGTAAGCGAGAATGGAAAATTCGTTCCTCGAGTTCCTCGGAATAT<br>GTTTAATATGTTCTTGATTACACCTTCCACGACGCCCCATTGAAGGGTCTCGGCTTTAATGGAGGAATTCGCT<br>ACACCGGTTTTACCTATGCGGACTATGTGGAGTCTTACAAAACGCCGGCGTATTATCTGTTTGACATTGGCGCA<br>CACTATGATTTTGAGGGAAATAATCCCTTCTCTCAAAGGTCTGCGTGCCAGTTGGCAATCTCAAATTTGGCCAA<br>TAAATATTATATTACTTCGTGCAATACCGCATATGTACTCTCGGTTATGCTCGAAAGTTTTACGGTAACGTGA<br>CGTATAGCTGGTGA |
| SEQ ID 7 | Reverse transcriptase family protein | GTGACGCCCGAATTGCTCCTCTCCAAGGTGCGGCTGCTGCGGTCGCCCAATGACGACGGCGCGTTCTTCGACCT<br>AGTCGGCAGTGTTCTTAATTGGTCCTGGGAGGAAAGAGACGAACGTCAATTCGCCCGCTTCAAGCAGCGCGCGG<br>GCATCCCTGAGTTCGATGGCGTCGCCCTTCCACAGGGTTTGGTTGCAGCTGGCTTCTTCGAACATCGTGCTG<br>CTTGATTTCGATCGGATCGTCATCGGACAGATTGGGAGAGAAGTTACAAACGGAGTGTGGCCTCCGGGACGCCTG<br>CCGGTACGTCGACGACATTAGACTGACCATAACAACTGCACCAGGTATTGACCCAAGAGAAGCTCAGGCGCGTG<br>TAATGGCGTGGCTTGGGCAACTCCTCACGGGGAGCTGTCCGGGCTTGGAATTCTCCCCGGAGAAGACGTCAACT<br>GCGTCGGTTGGAGGCGAGCAGATGCCGCTGGTTCGCCAATCCCGAAAGATGGAGCGCATCCAGACCGCGATTTC<br>CGGCGGCTTCGATGCCAGTGGTGGCGAGGAGGTGATCCACGCGATCGAAGCCCTCGTCCGATCCCAGCTAACGA<br>TCAACAGCGTCGAAGAGTCGCCTACCCCTCCCGGCTTGGACGGTACCCGATGTCAAAGACGAGACAGTCGGT<br>CGTTTCGCTGCTGGTCGGTTCAGAAAAACCTTTCGTTCATTGAGGCGCACTACTCGATGATCGACCTTACATGGA<br>GATTGCTGAATTCGGGGAGGAGACGTTCCGGCGCACCCGACTTTCGCAATCGGAGCTTGACGAGGAAGCACGCG<br>CATTTGCGCTAATCCTAGTCGAACGGTGGATACTCGATCCTTCGAATGTGCGGCTGCTGCGCGTCGCACTCGAC<br>CTCTGCCGTCCCGCCAACTCCTCAAGGAAGTACTGAAACTCTTTGAGCCCTATCTTGTCGGGAAGATCAGGGC<br>AATCACTAGCCGGCAAGTTGCATACTACTGCCTCGCCGAGATATTTCGAGCAGGGGCGACCGAGACGGGCTTCA<br>TTGACGATCCAGAGTGCCTTCCCGCTGCCGTCGATCTCGCCGGTTATAGATCTCTGCTTCTGGAGGCCGCAGTA<br>CGAGTGGCCCGGGGCGAAGCCGAACGTGTCCCGTGGTATCTCGCGCAACAAGCACTGCTTTACATTGCGGTCCA<br>CGATCCCCGGCTATCCAAGATCGAGGAATTTCAAGAACCAATCGATCCTATTGGCGCCTCGTCTCATTTCTGA<br>AAGGCGAACGCGACGTCTCTTCAGATCGCGAATTCGCAGTAGCCGCGGTGGTGAGCCGCAGGTCGTTCCTTTCG<br>AATGATCAGGCCGTGGATCTCGTCGGTCGGATGCTCACGCCAGAGCGGTTCGCCGAGGTGGCCGCGCGACAT<br>AGAATTCGCCCGCGATCTCTTTCGCGCCTCGACCGACACCTCACCGTTCCGGCAGGCATTGCCGAGGACTTGG<br>GGGTCGCCGAATGGTCCATGTCAGAGGGAAATGAGCTCTCTGCAAAGCTATATCCAAGGCAAAGGGCCTCTGAAT<br>CCGCTACGCAATGAGATCGGCGTACTCAGTTTTGCAGAGAAATTCATCTCCCATCTCCAAGAAGGAAATTTGCC |

TABLE 1-continued

| | | |
|---|---|---|
| | | GGAAGTCGTGACGCCGTCGACGACGCAGATAGCGGTACAGCAAGTGGGCAAATATGTCCGCGTCGAACGGGTGA<br>TCTTCAGATCGGCCCAGACAACGCCGACTTACCGGTCTATTTATACTGCTCCCAGATGGGCGCCGGAATCTCAA<br>CGCTGGCGCTTTCAGCTCGGTTATTTACTTCGCTTCATTCTTACTGCCAGAATAGACTTCAGCCTTCCAGTTAG<br>GCCGCCATCGTGGAAGGAAGGTAAACACATCTATCGGCCTACCAGAAGTCACTGGTTTCAGCGGCAATACGGCT<br>TCTATAATGGGCATGAGGCCTTCGGGGACGATTGGCTACCCATTTCGCAGTTCACTCAGGATCTTCTCTTCGAT<br>CTGCTCACCTGGCCCGGCTGCCGCACAAGTAGCCCGGATGTCGATCAGTTGTCCCTGGATGAAACGGCTGCTCG<br>AATCCGCGCAGCTCTCGTAGAAGCCACCGCTGCGATTGGCCCGGCTACAGGAACCCTGATGCTCAAGATCGATG<br>CACCTATTCCAGGTACCACATCGAAGGGGCGCCCGCTTCGGGCCTGCGTCGTCCAGTCGATCATGCCCGAAGCA<br>GAGGACTTCTCGGCTGCCGATCTGGAGATGCGCTCGCCGGCCCTTCGACGAAAGCACCGCAAACATCTGTCCAC<br>GGCATTGGCGGCGGTTGAGAAGATGTTGGATCTTCGCGAGACTCATAAGCCAGCCAGCAAGCGTCTCGACTGGC<br>TCATCCTACCAGAACTGTCTGTTCACCCGGATGACGTTGCCACCCACCTCGTGCCGTTCGCGCGAGCGTTCAAG<br>ACCGCGATCCTGGTCGGCATGGCCTACGAACAAGTCGTCACGGGAGAGCCGCTGATCAACTCGGCCCTCTGGAT<br>TATCCCGAGGATGGTGCGGGCATGGGCCTACAGACGGTGATCAGACGGCAGGGAAAACAGCACCTCTCTCCGA<br>TGGAACAGAAGTACGTCAAACCGGTCGAACTGATCACCGGATTCCGCCCGTGCCAGTGGCTGGTGGGGTACGAA<br>TGGGTCGAACAATCCGGCCAAAGACGCACTTTGGCTCACCGCGTCCATCTGCTACGATGCAACAGACCTGAAGCT<br>GGCGAGCGATCTTCGTGATCGCTCAGACGTGTTTGCGATCCCAGCCCTGAATCTCGACGTCGGCACCTTCGATC<br>AGATGGCGCAGGCGCTGCATTATCATATGTTCCAACTCGTGCTGATCGCGAACAACGGAGCTTATGGGGGCAGC<br>AATGCTCACGTTCCCAAGGGGGAGGCCTATCAACGCCAAGTGTTCCATACCCATGGCCAGCCCCAGGCTACAAT<br>TTCCTTTTTCGAGATCGACGATATCGAGGGCATGAAGCAGAGACACAAGCTCGGCGCTGGGAAGGAAGGCGGGT<br>GGAAATATCCACCTGCCGGCTGTCAAGTCTGA |
| SEQ ID 8 | DNA topology<br>modulation<br>protein | TTGATGCGCTTGTTCGTGACGGGGCCAACTGGCAGTGGAAAATCAACGCTGGCTGCAAAGTTGGCTCAAAGGGC<br>AGCTATACCACTGTTCCCGCTCGATGAAATTCATTGGGTTCGCCATCTCTCCGGGGATTGGCGGCGCGATCCTG<br>TTGAACGCCTGTCTATGCTCGGAGAGATTGTACAGCTCGATGCCTGGGTCATCGAAGGCGTGCAGTTCAAATGG<br>ACTGATATAGCGATAGAACGAGCAGACTGGATCGTCGTCCTCGATCCACCACGTTGGCGGAACATCGCTCGTAT<br>CCTGCGCGTTTCGTCAATCGCCGATGCTTTTCTGGGGCGGGCACCGTGGAACGGTAAAGGCTCTATTGGAGG<br>AGATGCGTTGGTCAGCCGACTACTATGGTCATGAACGCGGGTATGCTGTTCGAGAAGATTGGACAATCGCCAGAC<br>AAGCTCATCGTCGTACATGACGACAAGGGCGAACGCGCTTTGACCGAGGCTGTATTCGCGACTGCGTGA |
| SEQ ID 9 | Cycloisomal-<br>tooligosaccharide<br>glucano-<br>transferase<br>precursor<br>(EC 2.4.1.-) | ATGGCATATTGGATCAGGCTCTCGCTGGCCGTGTGGCCGCCCGATCAGCAACGTTGTAGCGAAGGCCGCGTAAT<br>GCGCCGCTATCTTTTCACAACCATTCTCTCGCTCTTACCGTCCCTTGCGGCGGCGGCATCCCTCCAAGGTCCGA<br>TTGTTTCGCATGTGCGGGATGATCGGGCTTTCTACCAGGCAGGCAATGTCGCGATGATTTCCGTGGAACTGACC<br>CCACTAGCCGCTTGGACGGGAGGCCATGTGGATCTAGCGATATGTTCGCGTGGGCAAGTCGTGGGCACGATTCA<br>GAGCCAAGCGGTCACCAGCATGGTGGCTGGGCGGACCAGACACTTCACTATCCCGTCACCGTTCCCAGTCTCC<br>ATGCTCATGGGTATCAGTTGGCTATCGCGGCCCTGAACAATGGGGACAGCGGGACAGCGTCCTGTACCGGGACA<br>GGCAGCACTTCCACGTCGCCGGCCGATGTGGCGTCAGGCGGCATCAACGTGGCCGCGAATGCCTGGGAAGACAT<br>CAACGAAGCATGGGTCGACGCGCCGACGCTCGGCGACGGCTCGCCGGCCCGGGTGATGGATAATCTCAGCCAGT<br>ATCACATCAACGCGGTGCAATTTTACGACGTGCTGTGGCGACATGACGAGCCGTATTCATCCGCCCGCAGTGG<br>CCGAACCTGGAAGGCGTAACGGTCACAAGGACCAATCTTCAGGCTTATATCAGCGCGGCGCATAGCCGCGGCAT<br>GGTGGCGCTCGCCTATAATCTCTGGAACGGAGCCTGGGCGGACTATGCAACTGTCAATCCGAAGGTCACGGCGG<br>CAATGGGGCTCTATGCTTCGTCCGGACAGAAACACCAACTGACCAACGGCGGGGGCTGGCTGTCCTGGGGGTGG<br>TCGACCGACCATATTGCTGAAATGAACCCGTTCAATGGCGACTGGGCCAGATGGCTAACCAGCCAGATCCAGAA<br>GACCATGTGGAATTTAGGATTCGACGCCGCGCATCTGGATACGTTGGGTGACCCTGGTGGTCAGCAATATGACG<br>GCGAGGGCCATCCGTTACCTGCTTTAGGAACGATTCTGGCAGACTTTGCGAATAATGTACAGGCTCAGACCGGG<br>GCACCAACTGACATCAACGCCGTTTCGGGTTGGAATACCACCGACCTTTACCTACGCGGTACGGGACCCAACCT<br>GTATATCGAACCCCATCCCGAATTCGGAAACACGCCGGGCTACGATGATTCCCGAAGCTTATGGGACATCAAAC<br>AGAAATACGTCGCGCCCGCTGATGACGGCGTTTTATCCGCAGCAGGTCCAGAGCGGTTCGCTGAGCACGTCC<br>TTTGCCGTCAAGGGTGAGAGTGTGAAGGTTTGCGACCCGACGTTAAAATCCGGATGCATAGCCAATAACCTCGG<br>CATTGAGTTGTTGCTCGGCCAGATTGCGCTCAATGGAGGCTCCAATATTACTCTTGGTGATTTTGATCATCTGA<br>TACCGGGGCATATTTCCCCCGTCCGACCCTTAAGATCGACGGTCCATTGCAGCAATATCTGGCGGATTACTAC<br>AACTGGTGGGTCGGAATGCGCGATCTGCTGCGTGTCGGCGTCATCTCATCCAATGAGAGGGAGTCCATCCGGAA<br>TGGAAACGGAGCCAGTATCGGCCAACCTTATGCCCAACCGGGAACCGTCTACTATCATCCCCTGATACGCGCTG<br>GCATCGCTGGTGAATTGGCGCTCACAAACATGATCGGGTTGCATTATAATCGGATTGACGACCCTGACGGCAAA<br>AACAATCCGACCCCGGTGAACAACCTGTCGATCGAGATGGAATTCTGGGAAGAAGCACACCGGGGGCATTGTA<br>CTATAGCGCGCCCGACATCAACCACGCGCTTCCCACAGCCCCTCACCTATAGGCTGAACGGAAACGGTAGCGTGA<br>TGTTTACGCTACCGACTCTCAAGACGGTGGCGCTTGTTTGGCTGGAAGGCACCAATTTCACCACTACGACCGAT<br>TACACGATCGGTACGGCGCAGGATGTGAGGGGTGGCACAGCAAACTTCTGGACGAACGGCAGCGGAGGAGGATGC<br>TACCGGATATCGTGCTGCTGTGGTCGCTCCGCACGCTGGGACAGCATCGATTTCGGAGCGGGTGTGTCAACGC<br>TAACGATGGTAACCCGAAGCCAACTCGGCGGACTGGTCGAATTTCGCCTGGATGCACCTGATGGACCAGTCATC<br>GCCCGTAATTATGTTCCTGCGTCTAGCGCCACGACAACAACCACTCAATTACGCAGGCCAGTATTCGGGACACA<br>TACCGTCTTCGCTAAAATTCCTGGTCGCGAGATTACGCTGATATCCTGGAAGCCATAA |
| SEQ ID 10 | Methyltransferase<br>(EC 2.1.1.-) | ATGATGGCTAACGACAATACCACTGAGGTGGTTGGTGCATTTGCGGTAAGTCATCCCAACTTGGCGCAAGGTTT<br>TACTTTTAGTAACAGCAGTCAACTAGATACGATTGCTTCTACTATTCATAAAAGCGGTTTGGAGACTTATGAAG<br>CTCCGACAACTAATATAATTATCGAACTGATCAGGAGTTCGTCTGGTCTTATTTTAGATGTGGGAGCGAATACC<br>GGTCTTTTTACGCTAGTCGCCGCAGCAGCCAACCCCCTGATCCGCGTCTGCTCTTTTGAGCCGCTTGCGAGTAT<br>TCGTGAACTTCTCAAGAGCAATATTGCTCTCAATCCGGAGCTTGCATCACGTATCGCTGTCGAGCCTGTCGGGT<br>TATCGAATGACAGGGGCACTTTCACTTTTTACGAAACGATCAACAATCGTGGCTTTGTCACGACGAGTTCATCG<br>CTTGAAAAAGCACATGCAGAGCGAATCGGCGATTTGTACGTCGAGCGCACTATCGAGACCGGACACTTGATGA<br>ATTCGGAGAAACGCTCGGGAATGCGAGCGTTCCGTTCGTCAAAATTGACGTTGAGGGACATGAGCATGCCGTTA<br>TCTCCGGTGGCGCCACTTTATCGCCAAGCACCGCCCTTTTCTTACTCTCGAAGTCCTGAGAGAGGCTAACACT<br>TTGAGTCTGGACCAGTTGGTGACCGAGTCCAACTACCTTGCCCTGGCAATGGCACCCGACGAATTGCGGCAGTG<br>CGAGCGTTTACGGTTTCATGACGACGCCTGGAATCATCTTTTGGTCCCCGCCGAAAAAGCGGAACGGCTATTTT<br>CGCTCTGCCGCCGACTTGGCTTGCAAATCGGGATCCGCTGA |

TABLE 2

| SEQ ID 11 | Transcriptional repressor; asserted_pathway: PF01381<br>Peptidase S24-like::PF00717 | ATGTCGAATTCCGAGCGCCCAATGCGCGATTTGTCGGACCTGGCAAAAAACCGACAAATAGAGCCGATGGTTAT<br>CAGGCTACGAGAAGTAGTGGATCGGACCGGAGGCGCGAAAGCTGTGGCCGCACGCACGGACATCCCTCTCAGCA<br>CACTTTCAGGTTACCTGTCGGGTCGGGAACTCAAGCTTTCCGTCGCGCGCAAGATCACGGAAGCCTGCCGGTGTC<br>AGTCTTGACTGGCTTGCGGCAGGAGAGGACGGACCTGCGGCCCGGGAATTCGGCAATGCCCGGCAGGCGGGTCC<br>CGAGTCGGTCGGAGTTTCTGAATTACGACGTCATTCTCTCCGCCCACCAGGGCGTCGACGGGGATAGTTCTTATA<br>TCGAAACGAGAATATCGATACCGCGGGATTTTCTCCCTTTGTCCATTCAGTCCAATACGGACAACATTTCGGCC<br>GTCACGGCGAAATGCGACAGCATGAATCCGATCATAGACGATGGAGACATTCTTTTAATAAGAACGGATGTGCA<br>TACGCTCACAAGTGGCAGCATCTATGCCCTGCGGGTAGAAAAACACCCTTCTGGTCAGGCGTCTGATCCTCAAGA<br>CCAACGGCAACGTCCAGGTCATCAGCGAGAACCCGCGTTACCCGACCGAGGAACTGAACGCCGAGGACGTTCGC<br>AGGATGGTCCAGGACGACGGCTTTCCGGCCAGGATCATCGGCCGGGTCATCGGCGCGCCGGTAGCCTGATTCC<br>ATAG |
| --- | --- | --- |
| SEQ ID 12 | outer membrane heme receptor | ATGCGCATCGTCCTCTTGCCCTGCCTCGTCGCGACCTCAATAAGTATGTTGGCGGTTTCCGCATCCTATGCTTG<br>GGCGGACAATAGCCCGTCGCCCCCCAGGACGAACAAACAGGCCAAATCGCGGCCGTTACATGCGCAGGGGACGC<br>GCAAAGCGGGCAGCGCCATCACCAGCCAGGATGAAGCGGTGGCTGTCGTGGGAACACGTGAGACATCGCATGGG<br>ATGGAGCAGAGCGTTACCCGTGCGACGATGGACAAGTTCGTGGCGGGGACCAGTCCCCTGCAGATTCTGTCGGC<br>CACGACACCGGGTGTCAATTTTGCCTCGGACGACCCGTTCGGCCTGGATACATGGGCGAACACATTTTATATTC<br>GCGGCTATTCCCAAAGCCAGTTGGGCATCACCCTGGACGGTATCCCGCTGGGCGATGCCCAGTTCATCAATTCC<br>AACGGCCTCGATATCAATCAGGCGATCATCCAGAACAATATCGGTCGCGTCGACATGTCGCAGGGTGGCGGTGC<br>GCTCGATGTCATGTCCGTCACCAACCTGGGTGGCGCGCTGCAATATTATTCACTCGATCCGCGCGACAAGGCTG<br>GTGGAGACATTTCACGACGTTCGGCAGCAACCAGACCTATCGCACGTACGTCAGCGCCCAGAGCGGCAAGCTC<br>AATCCCAGCGGGACGAAGTTCTATGCGTCGTACGCGCGCACCGATGCCGGGAAATGGAAAGGCGCCGGGGACCA<br>GTTCGAACAGCAGGCGAATTTCAAGATCGTACAGCCGCTCGGGCGTTACGGAAAACTGTCCGGATTCTTCAATT<br>ATTCCGAATTCGACCAGTATAATTACAGCGATTTGAGCCTGGAAATCATCCAGAAGCTCGGCCGGAACGTGGAT<br>TATTTCTATCCGAACTACAAAGCCGCGTATCAGGCTGCCGAGGGGATCTATCCCGCAGGCTATGCCAAGGTCGG<br>AGATGCCATGGACGTCTCCTATTACGATGGTGGCCAGGACCAGCGGAATTATCTTTCCGGCATCACGTCCACGA<br>TCGACCTGACGTCCCGCCTGCATCTGAAGACGGTGCTGTACGACCAGCAATCGGCGGGGACTACGAATGGACC<br>AACCCCTATGTGTCGTCGCCCTCGGGCGCGCCCATGATCCAGCAGGTCGGGCACACATCGATGACGCGCGTGGG<br>CGGGATTGGCGCGGTGCAGTACCAGATCGCCAATCATTCGCTTGAAACCGGCGTCTGGTACGAAAACAACGGAT<br>ATAGCTGGGCGCAACGGTACTACAACCAGCCGCTTCTGGGGGAGGGTACGCCCCGAAGCGCCACCGGACCGTAC<br>AACGATCCGTTCGCCACCGCATACGCCATGACCTTCAATACCAACAGTTTTCAATATTACCTGGAAGATTCCTA<br>CCGTATCTTGAAGACGCTGCCGGTGCACGCGGGCTTCAAATCCATGCTGACGACGACGTCGGGCGGCGCATCCT<br>ATAACAATCCCGTCTATACGGGCCAGGACACCCTGCCCAGTGGCAGCCTGACCACCGCCAGCGCCTTCCTGCCG<br>CATGTCAGCATCAACTGGAATTTCCTGCCCCGGAACGAACTGTTTTTCGACTTCGCGGAGAACATGCGCGCATT<br>CACCTATAATACATGGCAGAGCGGGAATGCATGGGGAGTCAATGAGATGCCCCAGAACCTGAAGCCCGAGACCA<br>CCTTCAATTACGAGGTCGGTTATCGATATAATTCCCGCTTCGTCACGGGCCTCGTCAATCTGTATCATATCGAT<br>TACAGGAACCGGCTGGCCACCATCACCACCGGCAGCCTGGTGAACGCCCACAATACCTATATCAACGTGGGGAA<br>CATGGCGATCTGGGGTGCCGATGCCGGCGTGACGGTGCGCCCGCTGCCGGGCCTCGAGATCTTCAACAGCGCCA<br>GCTACAACAAATCCACCTATGGGCAGGATGTATCCAGCGGCGGGGTAAATTATCCCATCGGCAAGCAGGAG<br>GCCGGCTATCCGCAATGGATGTACAAGGCCAACGTCTCGTACAGGTATGGCAACGCGAAGGTCAACTTCAACGT<br>CAACTATATGGGAAAGCGATACATCTCGTACATGAACGACGCCGCCGTGAACGGGTATTGGCTGGCATCGCTGT<br>CGGCGACGTATATCTTCAAAACCATTCCCCATCTCTCTCAGCTTGAATTCAATTTCGGCGTCTACAACCTGTTC<br>AACCAGGAATATATCGGCGGCATCGGCGGTTCTCACTGTCCGGTGACACGCAGCAACTCTTTGCCGGCGCGCC<br>ACGCCAGTTCTTCGGTACGCTGCACGCACGGTTCTAG |
| SEQ ID 13 | Levansucrase | GTGACGGCGCGGTCGTGGTTGCTCTGCAATCTGAAGAGTTTCCTTCAGGAGGATGGAATGGCGCATGTACGCCG<br>AAAAGTAGCCACGCTGAATATGGCGTTGGCCGGGTCCCTGCTCATGGTGCTGGGCGCGCAAAGTGCGCTGGCGC<br>AAGGGAATTTCAGCCGGCAGGAAGCCGCGCGCATGGCGCACCGTCCGGGTGTGATGCCTCGTGGCGGCCCGCTC<br>TTCCCCGGGCGGTCGCTGGCCGGGGTGCCGGGCTTCCCGCTGCCCAGCATTCATACGCAGCAGGCGTATGACCC<br>GCAGTCGGACTTTACCGCCCGCTGGACACGTGCCGACGCATTGCAGATCAAGGCGCATTCGGATGCGACGGTCG<br>CGGCCGGGCAGAATTCCCTGCCGGCGCAACTGACCATGCCGAACATCCCGGCGGACTTCCCGGTGATCAATCCG<br>GATGTCTGGGTCTGGGATACCTGGACCCTGATCGACAAGCACGCCGATCAGTTCAGCTATAACGGCTGGGAAGT<br>CATTTTCTGCCTGACGGCCGACCCCAATGCCGGATACGGTTTCGACGACCGCCACGTGCATGCCCGCATCGGCT<br>TCTTCTATCGTCGCGCGGGTATTCCCGCCAGCCGGCGGCCGGTGAATGCGGCTGGACCTATGGCGGCCATCTC<br>TTCCCCGACGGAGCCAGCGCGCAGGTCTACGCCGGCCAGACCTACACGAACCAGGCGGAATGGTCCGGTTCGTC<br>GCGTCTGATGCAGATACATGGCAATACCGTATCGGTCTTCTATACCGACGTGGCGTTCAACCGTGACGCCAACG<br>CCAACAACATCACCCCGCCGCAGGCCATCATCACCCAGACCCTGGGGCGGATCCACGCCGACTTAACCATGTC<br>TGGTTCACGGGCTTCACCGCCCACACGCCGCTGCTGCAGCCCGACGGCGTGCTGTATCAGAACGGTGCGCAGAA<br>CGAATTCTTCAATTTCCGCGATCCGTTCACCTTCGAGGACCCGAAGCATCCCGGCGTGAACTACATGGTGTTCG<br>AGGGCAATACCGCGGCCAGCGTGGCGTCGCCAACTGCACCGAGGCCGATCTGGGCTTCCGCCCGAACGATCCC<br>AATGCGAAACCCTGCAGGAAGTCCTGGATAGCGGGCCTATTACCAGAAGGCCAATATCGGCCTGGCCATCGC<br>CACGGATTCGACCCTGTCGAAATGAAGTTCCTGTCGCCGCTGATTTCGGCAACTGCGTCAATGACCAGACCG<br>AACGGCCGCAGGTGTACCTCCATAACGGAAAATACTATATCTTCACCATCAGCCACCGCACGACCTTCGCGGCC<br>GGTGTCGATGGACCGGACGGCGTCTACGGCTTCGTGGGTGACGGCATCCGCAGTGACTTCCAGCCGATGAACTA<br>TGGCAGCGGCCTGACGATGGGCAATCCGACCGACCTCAACACGGCGGCAGGCACGGATTTCGATCCCAGCCCGG<br>ACCAGAACCCGGGGCCTTCCAGTCCTATTCGCACTACGTCATGCCGGGGGGACTGGTTGAATCGTTCATCGAC<br>ACGGTGGAAAACCGTCGCGGGGTACCCTGCGGCCCACGGTCCGGGTGCGCATCGCCGAGACGCCGTCGCGGT<br>CGACCTGCGGTACGGCAATGGCGGCCTGGGCGCTATGGCGATATTCCGGCCAACCGCGCGGACGTGAACATCG<br>CCGGCTTCATCCAGGATCGTTCGGCCAGCCACGTCGGGTCTGGCGCGCAGGCGTCCACCAACAATGCCCAG<br>GTGCTGGCGCAGGTTCGCCAATTCCTGAACCAGTAA |

The invention claimed is:

1. A strain of *Gluconacetobacter diazotrophicus* (Gd) comprising nucleic acid encoding one or more expression products encoded by SEQ ID NOS 1 to 10 and a plasmid that is less than 27455 bp in size.

2. The strain of Gd according to claim 1, wherein the nucleic acid encodes at least three of said expression products.

3. The strain of Gd according to claim 1, wherein the nucleic acid encodes at least five of said expression products.

4. The strain of Gd according to claim 1, wherein the nucleic acid encodes all of said expression products.

5. The strain of Gd according to claim 1, which comprises one or more sequences with at least 90% sequence identity to any of SEQ ID NOS 1 to 10.

6. The strain of Gd according to claim 1, which comprises at least one of SEQ ID NOS 1 to 10.

7. The strain of Gd according to claim 1, which comprises at least three of SEQ ID NOS 1 to 10.

8. The strain of Gd according to claim 1, which comprises at east five of SEQ ID NOS 1 to 10.

9. The strain of Gd according to claim 1, which comprises all of SEQ ID NOS 1 to 10.

10. The strain of Gd according to claim 1, wherein the plasmid is in the range of 17.5 to 17.6 kbp in size.

11. The strain of Gd according to claim 1, wherein the plasmid is about 17566 bp in size.

12. A composition comprising the strain of Gd according to claim 1 and at least one agriculturally acceptable carrier.

13. The composition according to claim 12, which is suitable for coating a seed.

14. A seed having a coating thereon, wherein the coating comprises the strain of Gd according to claim 1.

15. A plant or seed comprising the strain of Gd according to claim 1.

16. The plant or seed according to claim 15, wherein the strain of Gd is located intracellularly within.

17. A method for producing a plant product, the method comprising growing the plant or seed according to claim 15 and obtaining the plant product therefrom.

18. A method for enhancing the nitrogen-fixing ability of a plant, said method comprising applying the strain of Gd according to claim 1 to the plant, an environment around the plant, or a seed that gives rise to the plant, such that the strain of Gd colonizes the plant.

19. The method of claim 18, wherein the strain is applied to a wound of the plant, a growth medium of the plant, or the surface of the seed.

20. A strain of *Gluconacetobacter diazotrophicus* (Gd) deposited with CABI in the United Kingdom under the Budapest Treaty with deposit accession number IMI 504958.

* * * * *